(12) United States Patent
Freudenthal

(10) Patent No.: US 10,004,598 B2
(45) Date of Patent: *Jun. 26, 2018

(54) IMPLANTABLE DEVICE FOR USE IN THE HUMAN AND/OR ANIMAL BODY TO REPLACE AN ORGAN VALVE

(71) Applicant: PFM MEDICAL AG, Cologne (DE)

(72) Inventor: Franz Freudenthal, La Paz (BO)

(73) Assignee: PFM MEDICAL AG, Cologne (DE)

(*) Notice: Subject to any disclaimer, the term of this patent is extended or adjusted under 35 U.S.C. 154(b) by 0 days. days.

This patent is subject to a terminal disclaimer.

(21) Appl. No.: 15/337,676

(22) Filed: Oct. 28, 2016

(65) Prior Publication Data

US 2017/0042675 A1 Feb. 16, 2017

Related U.S. Application Data

(62) Division of application No. 14/421,638, filed as application No. PCT/EP2013/066385 on Aug. 5, 2013, now Pat. No. 9,655,721.

(30) Foreign Application Priority Data

Aug. 15, 2012 (DE) .......................... 10 2012 107 465

(51) Int. Cl.
*A61F 2/06* (2013.01)
*A61F 2/24* (2006.01)
(Continued)

(52) U.S. Cl.
CPC .......... *A61F 2/2418* (2013.01); *A61F 2/2403* (2013.01); *A61F 2/2409* (2013.01);
(Continued)

(58) Field of Classification Search
CPC ........ A61F 2/24; A61F 2/2418; A61F 2/2403; A61F 2/2409; A61F 2/2439; A61F 2/2475
See application file for complete search history.

(56) References Cited

U.S. PATENT DOCUMENTS 6,669,724 B2   12/2003   Park et al.
8,062,355 B2   11/2011   Figulla et al.
(Continued)

FOREIGN PATENT DOCUMENTS

DE   10334868   3/2005
EP   1849440    10/2007
(Continued)

OTHER PUBLICATIONS

International Search Report from corresponding PCT Appln. No. PCT/EP2013/066385 dated May 2, 2014.

*Primary Examiner* — Alvin Stewart
(74) *Attorney, Agent, or Firm* — Grossman, Tucker, Perreault & Pfleger, PLLC

(57) ABSTRACT

The invention relates to an implantable device for use in the human and/or animal body to replace an organ valve, comprising a main body having a first end and a second end, wherein the first end and the second each have an opening to provide a fluid connection through the main body between the first end and the second end; a first membrane element arranged inside or at one end of the main body, wherein the membrane element is formed in such a manner that it allows the fluid connection through the main body in a first flow direction and blocks the same in a second flow direction opposite the first flow direction; wherein the main body has a large ratio of length to transverse expansion along the longitudinal axis of the main body in a first operating state (primary form) and a smaller ratio of length to transverse expansion along the longitudinal axis of the main body in a second operating state (secondary form); and wherein the main body can be reversibly transferred from the secondary form to the primary form counter to elastic material forces by the application of a force; and wherein the main body is formed from a single wire-like element or from a plurality of wire-like elements connected to each other by means interlocking winding and/or twisting and/or weaving in the manner of a woven and/or layered fabric and/or net.

42 Claims, 15 Drawing Sheets

(51) Int. Cl.
  *A61F 2/90* (2013.01)
  *A61F 2/856* (2013.01)
  *A61B 17/00* (2006.01)

(52) U.S. Cl.
  CPC ...... *A61F 2/90* (2013.01); *A61B 2017/00592* (2013.01); *A61B 2017/00606* (2013.01); *A61F 2/856* (2013.01); *A61F 2210/0004* (2013.01); *A61F 2210/0014* (2013.01); *A61F 2210/0076* (2013.01); *A61F 2220/0008* (2013.01); *A61F 2230/005* (2013.01); *A61F 2230/0069* (2013.01); *A61F 2230/0078* (2013.01); *A61F 2250/0018* (2013.01)

(56) References Cited

U.S. PATENT DOCUMENTS

| | | | |
|---|---|---|---|
| 8,353,955 | B2 | 1/2013 | Styre et al. |
| 8,696,737 | B2 | 4/2014 | Gainor |
| 9,655,721 | B2 * | 5/2017 | Freudenthal .......... A61F 2/2418 |
| 2002/0183828 | A1 | 12/2002 | Park et al. |
| 2005/0060029 | A1 | 3/2005 | Le et al. |
| 2006/0224183 | A1 | 10/2006 | Freudenthal |
| 2006/0276874 | A1 | 12/2006 | Wilson et al. |
| 2008/0077234 | A1 | 3/2008 | Styre |
| 2008/0103586 | A1 | 5/2008 | Styre et al. |
| 2008/0319538 | A1 | 12/2008 | Styre |
| 2009/0198315 | A1 | 8/2009 | Boudjemline |
| 2011/0160836 | A1 | 6/2011 | Behan |
| 2011/0208293 | A1 | 8/2011 | Tabor |
| 2012/0010697 | A1 | 1/2012 | Shin et al. |
| 2012/0136430 | A1 | 5/2012 | Sochman et al. |
| 2015/0216653 | A1 * | 8/2015 | Freudenthal .......... A61F 2/2418 623/2.17 |
| 2017/0042675 | A1 * | 2/2017 | Freudenthal .......... A61F 2/2418 |

FOREIGN PATENT DOCUMENTS

| | | |
|---|---|---|
| FR | 2874813 | 3/2006 |
| WO | 2008/100599 | 8/2008 |
| WO | 2011072084 | 6/2011 |
| WO | 2011143263 | 11/2011 |

* cited by examiner

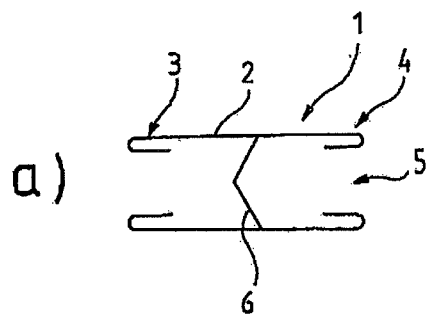
a)
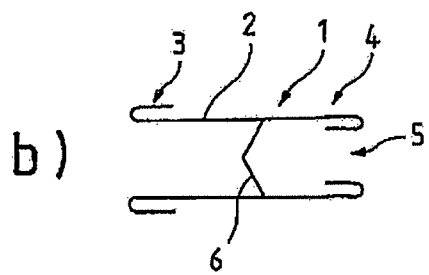
b)
Fig. 3
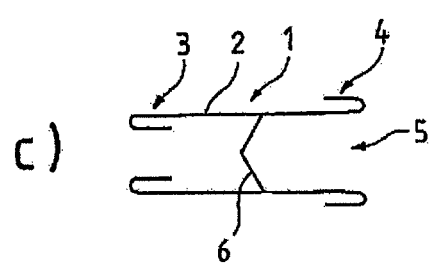
c)
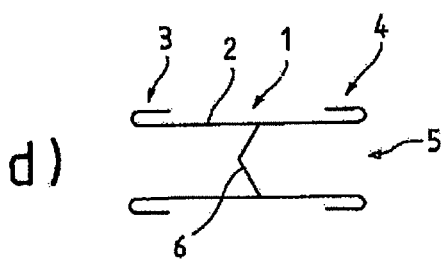
d)

IMPLANTABLE DEVICE FOR USE IN THE HUMAN AND/OR ANIMAL BODY TO REPLACE AN ORGAN VALVE

CROSS REFERENCE TO RELATED APPLICATIONS

This application is a divisional of U.S. patent application Ser. No. 14/421,638 filed on Feb. 13, 2015 which is a U.S. National Phase Application under 35 U.S.C. § 371 of International Patent Application No. PCT/EP2013/066385 filed Aug. 5, 2013, which claims priority to German Application No. 10 2012 107 465.8 filed Aug. 15, 2012, the disclosure of which are incorporated by reference herein in their entirety.

FIELD OF THE INVENTION

The invention relates to an implantable device for use in the human and/or animal body to replace an organ valve comprising a main body having a first end and a second end, wherein the first end and the second end each have an opening to provide a fluid connection through the main body between the first end and the second end; a first membrane element arranged inside or at one end of the main body, wherein the membrane element is formed in such a manner that it allows the fluid connection through the main body in a first flow direction and blocks the same in a second flow direction (opposite the first flow direction); wherein the main body has a large ratio of length to transverse expansion along the longitudinal axis of the main body in a first operating state (primary form) and a smaller ration of length to transverse expansion along the longitudinal axis of the main body in a second operating state (secondary form); and wherein the main body can be reversibly transferred from the secondary form to the primary form counter to elastic material forces by the application of a force.

BACKGROUND

Such implantable devices to replace an organ valve in the human and/or animal body are known from the prior art. In the past it was usual to replace particularly heart valves with an open-heart surgery, which is not an unperilous operation, especially for older patients. Thus, devices to replace a heart valve have been developed, which can be inserted without an open-heart surgery via a catheter at the desired location in the heart. For example, it is known from EP 0 592 410 to provide a compressible resilient valve, which is mounted on a resilient stent, wherein the commissural points of the elastic collapsible valve are mounted on the cylinder surface of the elastic stents. The elastic compressible valve is a biological, trilobate valve. The stent comprises a stainless steel wire folded in a number of loops and circularly bent together and welded together. The stent includes two or more closed rings that are connected to each other to form a cylindrical structure. Three of the loops in the outer ring are formed with a greater height than the other loops, to form tips at which the commissural points of the biological valve are attached. The cylindrical surface of the stent can also be closed. Due to the pipe or ring shape of the stent only a relatively poor anchorage at the implantation site, particularly in the aorta and the heart, is possible.

A more advanced anchoring for a heart valve replacement is described in DE 101 21 210 A1. According to this document, a intraluminal anchoring element is shaped differently to the cylinder shape, so that it is at least partially connected in the use position positively to the aorta. The intraluminal anchoring element of this document has therefore radially extending extensions at the exit of the heart (behind the original aortic valve). Moreover, it is curved and adapted to the curved shape of the aorta. The anchoring element is for example composed of a grid-like, loop-shaped or helical-shaped and built of a thread structure or filaments and may include several meandering, ring-forming thread structures. The individual ring-forming structures are interconnected or connected together by gluing, soldering, welding, etc. This embodiment of a heart valve replacement has the disadvantage that the anchoring element is designed very long, and thus must be placed very deep into a blood vessel or the heart. Although openings are provided for the connections to different coronary arteries, it can occur due to the length of the anchor element that they are partially covered by the anchoring element, which can result in a blockage of the blood flow or blockage of the connections to the coronary arteries.

From EP 1057460 A1 or the abstract of JP 2001/000460 A it is known, to provide a heart valve replacement device comprising a stent, wherein the stent is expandable in the radial direction of the blood vessel and a biological valve is attached to the stent. The stent valve arrangement is applied to the expanding part of a balloon catheter and inserted into the body of a human. The stent is composed of a plurality of sections, which are formed of wire. The individual wire sections are welded together. By means of the balloon catheter the stent is expanded at the implantation site to the desired diameter, which is done in two stages. After expansion of the stent at the implantation site, the diameter of the balloon catheter is reduced and the catheter is removed. The pulmonary valve replacement device remains in the pulmonary artery, touching the artery wall. A disadvantage of this heart valve replacement device is that a balloon catheter must be used to expand the stent. In addition, the stent keeps its position only due to its expanded form within the vessel or artery. However, it has been shown that this type of heart valve replacement devices suffer with problems due to shifting of the stent within the vessel, especially since, in case of a non-precise positioning, the connections to coronary arteries can be blocked, causing an at least partially closing of these connections and thus can lead to a stagnant blood flow. In addition, an incorrect positioning is problematic because using the balloon catheter, the stent can be expanded, however, cannot be reduced again in diameter.

From U.S. Pat. No. 5,855,597 it is also known to cut out star-shaped elements and assemble them to a stent. An aortic valve of a flexible, biocompatible material is inserted into a central opening of the joined star-shaped elements. Via a catheter system the stent is delivered to the desired implantation site. The star-shape achieves a fixation within the aorta, but there also exists a risk of injury, especially if the blood vessel is easily vulnerable, especially perforatable, due to age or other health conditions of the patient.

From U.S. Pat. No. 6,482,228 B1 for example an aortic valve replacement is known, with a stent and offset therefrom, but linked with it, a rotor-shaped valve replacement. This is placed over the original valve. The stent consists of several connected rings of wave-like bent wire. A disadvantage is the structure of a stent with an offset rotor-shaped aortic valve replacement for a placement behind the original aortic valve. The structure is on the one hand very complicated and on the other hand there is a risk that the rotor is disengaged from the stent. Furthermore, the rotor is positioned in the aorta and essentially secured in a longitudinal direction without a further fixation by the stent. The aortic valve replacement therefore does not provide a firm and stable unit.

As a heart valve replacement from the state of the art ring-shaped devices are known, which have post elements projecting at three points out of the ring. These can either be looped, as disclosed in WO 97/46177, or consist of a solid material, such as described in U.S. Pat. No. 4,816,029, DE 196 24 948 A1 and DE 35 41 478 A1. However, these ring-shaped valve replacement devices are all not implantable via a catheter because they cannot be collapsed to a corresponding small size.

From DE 103 34 868 a further implantable device for use in a human and/or animal body to replace an organ valve is known. The disclosed implantable device comprises a main body having a first and a second end with openings and a membrane element with at least one opening. The device has in a first operating state a large ratio of length to transverse extent along an axis and in a second operating state a smaller ratio of length to transverse extent along the axis, wherein the device can be reversely transferred by applying a force against elastic material forces from the secondary form into the primary form. Furthermore, the implantable device includes at least one of the two ends of the main body an extending anchoring portion for anchoring the device in an organ and/or a vessel. The main body of the implantable device according to DE 103 34 868 A1 is integrally formed and for example cut out and/or punched out and/or separated out by another separation process of a single piece of material. This results in the disadvantage that the implantable device has a relatively high rigidity and must be treated chemically and/or mechanically in at least a partial region of the main body for generating different stiffnesses, and in particular etched, electro-polished, micro-grinded or otherwise treated. Furthermore, there is a risk by an excessive post-treatment of the main body, that the individual elements of the main body, in particular the struts formed therefrom, be damaged by a transfer of the implantable device from the primary form to the secondary form.

The object of the present invention is to provide an implantable device to replace an organ valve, which has a high flexibility, without the risk that the individual elements of the implantable device will be damaged by a deformation. In particular, the invention has for its object to provide an implantable device which has different stiffness in different areas.

The object is solved by an implantable device for use in the human and/or animal body to replace an organ valve, comprising a main body having a first end and a second end, wherein the first end and the second end each have an opening to provide a fluid connection through the main body between the first end and the second end; a first membrane element arranged inside or at one end of the main body, wherein the membrane element is formed in such a manner that it allows the fluid connection through the main body in a first direction and blocks the same in a second flow direction opposite the first flow direction; wherein the main body has a large ratio of length to transverse expansion along the longitudinal axis of the main body in a first operating state (primary form) and a small ratio of length to transverse expansion along the longitudinal axis of the main body in a second operating state (secondary form); and wherein the main body can be reversibly transferred from the secondary form to the primary form counter to elastic material forces by the application of a force; and wherein the main body is formed from a single wire-like element or front a plurality of wire-like elements connected to each other by means of interlocking winding and/or twisting and/or weaving in the manner of a woven and/or layered fabric and/or net.

By forming the main body of a single wire-like element or a plurality of wire-like elements connected to each other by means of interlocking winding and/or twisting and/or weaving in the manner of a woven and/or layered fabric and/or net an implantable device is created, which has a high flexibility and at the same time ensures a secure fit at the implantation side. In the secondary form the implantable device for example conforms to a vessel wall. Because of the elastic material forces a force acts in a radial direction, which secures the implantable device at the implantation site. Since the main body is reversibly transferable from a primary form into a secondary form, it can be transported to the implantation site via a catheter without any problems. At the time of leaving the catheter the implantable device unfolds from the primary form into the secondary form, whereby the diameter of the main body increases and the length is usually reduced. Because of the possibility of a reversible transfer from the primary into the secondary form and vice versa from the secondary into the primary form, in contrast to the stent according to EP 1 057 460 A1, a retrieval of the device into the catheter is possible, if during the implantation is discovered that the implantation does not orderly proceed, particularly that the implantable device is not correctly positioned to the connection to corona vessels and/or to the native heart valve and/or the aorta as well as the heart ventricle. Because of the single wire-like elements or the plurality of wire-like elements connected to each other, which forms the implantable device by means of interlocking winding and/or twisting and/or weaving in the manner of a woven and/or layered fabric and/or net the advantage results, that the inventive implantable device has a high flexibility, without the risk that single elements of the implantable device break during the transfer from the primary form into the secondary form or from the secondary form into the primary form. The single wire-like design of the implantable device, particularly of the main body, has the further advantage that no connection points, for example welding points, between single elements of the main body are present, which could break easily. Especially such a break of single elements of an implantable device can lead to sharp edges protruding out of the device, which could damage or perforate a vessel wall, particularly an aorta. The structure of the main body can be designed more uniformly by an integral embodiment as it is possible in case of connecting separate ring-like elements, as known from the prior art. An implantable device built by a plurality of wire-like elements connected to each other has the advantage, that the implantable device can be easily manufactured automatically.

In a variant of the invention the implantable device is formed stent-like, wherein the first end and/or the second end is folded on each other to a double-layer in the second operating state (secondary form). Because of the double-layer the force acting in the radial direction during the transfer from the primary form into the secondary form is increased, whereby the fixing of the implantable device at the implantation site is improved, without a negative impact on the inner diameter (gate-way) of the implantable device. According to an advantageous variant the double-layer of the first end and/or the second end is formed by a backfolding into the implantable device and/or outwardly onto the implantable device.

Pursuant to a variant of the invention the main body has in the second operating state (secondary form) at the first end and/or second end at least one radially outwardly of the main body extending anchoring member for anchoring the device in an organ and/or in a vessel. Thereby an implantable device to replace an organ valve is created, which has, due to the use of at least one radially outwardly extending anchoring element at one end of the main body, a particular well fixing in the vessel and/or organ. In case of using the implantable device as a heart valve replacement the one end with the radially outwardly extending anchoring element can for example extend into the left ventricle and adhere there, and the other end of the main body can confirm to the wall of the aorta. Thereby the implantable device or the main body can be built much shorter than for example possible with a stent according to DE 101 21 210 A1.

SUMMARY

Advantageously the at least in a radial direction of the main body extending anchoring member is in the second operating state (secondary form) at the first end and/or second end located and circumferentially provided at the circumference of the main body at the first end and/or second end. Alternatively single radially extending anchoring members at the circumference of the main body can be provided. Depending on the implantation site the one or the other variant can be preferred, whereby the choice particularly depends on the space and a potential stenosis in a vessel caused by a calcium deposit or similar.

In a variant of the invention the implantable device has areas of different rigidity. These areas of different rigidity can be for example formed by differently interlocking winding and/or twisting and/or weaving of the single wire-like element or by a wire-like element with different cross-sections, particularly round, oval and/or polygonal. Particularly preferred is an area with lesser rigidity between areas with higher rigidity. Particularly preferred the area with lesser rigidity is located at the main body outside of the at least one anchoring member. Due to the areas with different rigidity bendings at the implantation site can be replicated, like for example the bending of an aorta. To guarantee a good fixing at the implantation site the area of the at least one anchoring member, thus the first and/or second end of the main body, preferably has a higher rigidity as one or more areas located there between. Over the length of the main body multiple areas with different rigidities can be provided, in case the outer conditions, particularly the aorta or the heart ventricle, require this. The distribution of rigidities over the main body can be adapted to a particular patient and his heart or the spatial conditions at the implantation site.

Generally it is possible that the implantable device according to the invention is adapted to each patient and/or to provide a standard shape, which is substantially usable for the majority of patients. Particularly at a basic form variable adaptable areas can be provided, which enables an adaption in the majority of exceptional cases. Thereby the costs of production of the implantable device can be reduced because real custom-made implants are infrequent.

In a variant of the inventive implantable device the main body has at least one opening in its circumferential wall, to provide a fluid connection between the inner of the main body and a vessel of the human and/or animal body. At the implantation site the inventive implantable device is in the secondary form for example located in such a way, that the at least one anchoring member extends into the heart ventricle, where it is anchored, and the remaining part of the main body, which is generally cylindrical, extends into a vessel, like e.g. the aorta, wherein the remaining part of the main body retains at the aorta wall. Through the at least one opening in the circumferential wall of the main body a fluid connection to an outgoing vessel, e.g. from the aorta of the human or animal body, can be provided, like for example a coronary artery. Advantageously the at least one opening has a diameter corresponding to a coronary artery, such that a blood flow in this area is not restrained.

In a particularly advantageous variant of the inventive implantable device it has two openings in its circumferential wall, which in the implanted state of the device are arranged in such a way, that the two openings overlap with coronary arteries.

According to a further variant of the invention the at least one opening in the circumferential wall of the main body is located outside of the at least one anchoring member, so that the function of the anchoring member is ensured. The implantable device according to the invention is therefore advantageously located inside the human or animal body in such a way, that the anchoring member does not block outgoing vessels of the human or animal body.

In a particularly preferred variant of the inventive implantable device the at least one opening in the circumferential wall of the main body is built by a further winding and/or twisting and/or weaving of the single wire-like element of the main body, wherein by the further winding and/or twisting and/or weaving of the single wire-like element of the main body in the area of the at least one opening in the circumferential wall of the main body a wider mesh size is achieved compared to the remaining parts of the circumferential wall of the main body. Advantageously the wider mesh size is built in such a way that in areas of outgoing vessels no element of the further winded, twisted or weaved main body is located.

According to a further variant of the invention the implantable device comprises at least one radio-opaque marker, particularly in the form of a marker tag, marking or marker wire. The radio-opaque marking is particularly located in the area of the main body. Thereby it is possible, to check the positioning during the implantation, particular with respect to outgoing coronary arteries, using a monitor or such a like. For this particularly an angiography or magnetic resonance tomography are suitable, which can display an axially precise positioning of the implantable device, which is preferably an aortic valve replacement. The markings can be provided at different positions of the main body or the implantable device, particularly in areas of the openings of the main body.

Advantageously the implantable device according to the invention completely or partially consists of a shape memory material, particularly of nitinol or a plastic with memory shape effects.

A further variant of the invention provides that the implantable device completely or partially consists of an absorbable material.

In a further variant of the invention the first membrane element consists of a synthetic or biological material, particularly of polyurethane.

According to a further preferred variant of the invention the first membrane element has a coating for establishing a biostability. The coating for establishing a biostability is preferably a titanium coating.

Main body and first membrane element of the implantable device are according to a variant detachable or inseparable connected or connectable to each other, particularly by gluing, welding, sewing, fusing, dip coating or another joining technology.

It is particularly advantageous that the first membrane element of the implantable device has a ring portion and a valve portion connected to the ring portion. Preferably the valve portion comprises three leaflet elements. Thereby particularly a natural valve can be reproduced. By providing a ring portion a good anchoring at the main body of the implantable device is possible. The main body consists particularly of a biocompatible material, preferably of a metal or a metal alloy particularly of stainless steel or plastic, like polycarbonate, and particularly of a memory shaped material like nitinol. The first membrane element preferably consists of a synthetic or biological material, particularly of polyurethane. Main body and first membrane element can be detachable or inseparable connected or connectable to each other. A connection of main body and first membrane element can therefore be achieved by gluing, welding, sewing, fusing, dip-coating or another joining technology. The ring portion of the first membrane element is preferably chosen with such a width, that a good anchoring at the main body is achievable. Since the first membrane element consists generally of a very thin material the ring portion can e.g. attached to or inserted into the main body as a thin tube. In this connection particularly a dip coating of the main body or applying a thin membrane to the inside or outside of the main body are suitable. Through this a protection against shifting of the first membrane element with respect to the main body is achieved.

The implantable device according to the invention is particular useable in adult cardiology, wherein preferably in connection with the higher probability of aortic valve insufficiency due to higher age. The inventive implantable device can also be used to replace a tricuspid valve, a pulmonary valve or a bicuspid valve (mitral valve).

The first membrane element of the implantable device according to the invention is located in the second operating state (secondary form) at the first end of the main body, at the second end of the main body or between the first end and the second end of the main body, preferably centrally between the first end and the second end of the main body along the longitudinal axis of the main body. The implantable device according to the invention has according to a variant of the invention in the second operating state (secondary form) at the first end and/or the second end at least a second membrane element, to partially close the opening at the first end and/or second end for fluids. Advantageously the first membrane element and the second membrane element are located adjacent to each other at the first end of the main body or the second end of the main body. The second membrane element is used to close the connection between the first membrane element and the main body for fluids, so that in this area of the connection between the first membrane element and the main body no fluids can pass.

Preferably the implantable device according to the invention is relocatable and/or explantable. The relocation or explantation is achieved in that the implantable device is reversibly transferable from the primary form into the secondary form and vice versa from the secondary form into the primary form. Thereby the implantable device according to the invention can e.g. be retracted into the catheter during the implantation in case it is recognized that the implantation does not proceed properly, particularly that the implantable device is not properly located with respect to the connections to the coronary vessels and/or the natural heart valve and the aorta as well as the heart ventricle.

In a preferred variant of the inventive implantable device the device is in a second operating state (secondary form) between the first end and the second end of the main body at least partially, preferably completely, deformable in a radial direction, such that the main body can adapt to a vessel wall and/or circumference of an opening and/or edge of a defect organ valve. Due to the fact that the main body adapts during the implantation to a vessel wall and/or circumference of an opening and/or the edge of a defect organ valve it is achieved, that the inventive implantable device after the implantation does not autonomously replace itself, for example caused by the pumping action of the heart. Furthermore is achieved, that the implantable device centres itself in the opening of the human or animal body.

For example the inventive implantable device is inserted during the implantation into the human and/or animal body such into the area of the heart valve, particularly the aortic valve, that the natural valve is pressed against the vessel wall during the transfer of the implantable device from the first operating state (primary form) into the second operating state (secondary form) and fix thereby the implantable device. In general it would be possible to place an implantable device into a previously implanted device, wherein the first membrane element of the previously implanted device is also pressed against the wall of the main body. Such implantation of a further implantable device into a previously implanted device could be reasonable in case for example of a reduced stability or flexibility of the first membrane element. Furthermore it is generally possible after removal of a natural valve, particularly by operation, to insert at this location an implantable device including a membrane element as a valve replacement. Particularly in case of a high calcification of the natural heart valve it can be advantageous to remove the heart valve completely because it is usually mostly immobile. In such a case it would be difficult to press the natural valve to the vessel wall. Furthermore a narrowing would remain in this area which is also not desired because of the reduction of the flow cross-section and the resulting higher pressure, which would result in health problems for the patient. In case of a heart valve insufficiency, the inventive implantable device can alternatively be implanted in the insufficient valve, for example the aortic valve or mitral valve without previously removing the natural valve.

For example the inventive implantable device can be introduced into the body via the carotid artery or axillary artery, which results in comparison to an implantation via the inguinal region of the patient to a reduced implantation distance.

The main body of the implantable device is preferably aligned in such a way that the projecting anchoring member at the first end protrudes into the heart ventricle, for example the left heart ventricle, and the remaining part of the main body clamps to the vessel wall, for example the wall of the aorta. Thereby a particularly good fixation and stable arrangement is achievable. The dimensions of the at least one anchoring member and the main body can be individually adapted to a patient, depending on the anatomy of the particular patient. Additionally the dimension of the projection of the at least one anchoring member can be chosen individually. Generally also a standardization is possible, according to which the anchoring member projects in such a way that most patients with such a type of main body or implantable device can be attended.

According to a variant of the invention the multiple to each other connected wire-like elements consist of a single wire, a wire strand of at least two single wires and/or a multiple wire, particularly the implantable device consists in areas with different rigidity of different wire-like elements, particularly of a single wire, a wire strand of at least two single wires and/or a multiple wire.

The single wire-like element of the inventive implantable device consists in an inventive variant of a single wire, a wire strand of at least two single wires or a multiple wire. The wire cross-section can be for example round, oval, semi-circled, quadratic or rectangular and also vary over the length of the wire-like elements, particularly in the area with different rigidity. The single wire-like element can if necessary be wrapped with platinum or gold or wolfram or supplied with platinum or gold rings, to enhance the X-ray contrast. In case of a wire strand preferably single wires of platinum or gold can be added into the wire strand to enhance the X-ray contrast. Particularly the usage of wire strands or a multiple wire has the advantage that the implantable device according to the invention is especially flexible with sufficient stability.

According to the invention the main body is formed by means of interlocking winding and/or twisting and/or weaving in the manner of a woven and/or layered fabric and/or a net. By the interlocking winding and/or twisting and/or weaving of the single wire-like element a tube-like element in the first operating state (primary form) is built. Both ends of the single wire-like element are located at the first end or the second end or in a side surface of the main body. Thereby on the one hand the risk of injury for the patient into which the implantable device is implanted is reduced and on the other hand the stability of the main body is enhanced.

According to a variant of the inventive implantable device the at least one anchoring member is in the second operating state (secondary form) disc-shaped or umbrella-shaped. Alternatively the one or a further anchoring member is bulgy and/or curved. After the implantation of the inventive device the disc-shaped or umbrella-shaped anchoring member rests for example against the inner wall of the heart and the remaining cylindrical part of the main body extends through the opening, which should be supplied with the valve device, to a vessel. The disc-shaped or umbrella-shaped anchoring member is partially deformable, so that it can better conform to the inner wall of the heart.

In a further variant of the inventive implantable device the main body has in the second operating state (secondary form) two anchoring members each extending in a radial direction of the main body. For example the first anchoring member is located at the first end and the second anchoring member is located at the second end of the main body in a second operating state (secondary form). The main body has an intermediate member between the first anchoring member and the second anchoring member, which has a smaller diameter than the first anchoring member and the second anchoring member. The diameter of the two anchoring members is equal or different. An implantable device with a first anchoring member and a second anchoring member, wherein the anchoring members are differently sized can be built for example such that the first anchoring member is located in the heart ventricle and fixes there in the second operating state (secondary form) at the inner wall of the heart and the second anchoring member is located in the second operating state (secondary form) at the inner wall of a vessel e.g. an aorta. The first anchoring member is therefore larger than the second anchoring member because inside the heart ventricle is more available space than in a vessel. An implantable device with two anchoring members, wherein both anchoring members are equally sized, can for example be used in a wall of an organ or a vessel, wherein the opening is closed by the valve device in one flow direction and in the other flow direction a fluid connection is provided. Such an embodiment, for example a double umbrella-shape, enables a firm seat in the opening of the organ or the vessel.

In a particularly preferred variant of the invention the at least one anchoring member in the second operating state (secondary form) of the main body has a first sub-portion and a second sub-portion, wherein the first sub-portion extends in a radial direction of the main body outwardly and the second sub-portion is folded backwards in a radial direction of the main body inwardly or outwardly, particularly in such a way, that the first sub-portion and the second sub-portion are folded onto another to a double-layer. Alternatively is the at least one anchoring member coiled in the second operating state (secondary form) of the main body, particularly helical. Preferably is the backfolding or coiling of the at least one anchoring member directed towards the middle of the main body. The anchoring member has therefore a backfolding or coiling which is directed towards the middle of the main body. Thereby a better fixation of the inventive device is achieved. Furthermore, the anchoring member is in the area of the backfolding or coiling and the resulting double-layered design at least partially deformable, so that the anchoring member can better conform to an organ or vessel wall.

In an advantageous variant of the implantable device the material concentration and/or material thickness within the implantable device is in sections differently. In a preferred variant the material quantity of the rim area of the implantable device and/or at the rim area of the at least one anchoring member is adapted to the desired mechanical properties, particularly a material concentration at the rim area of the implantable device and/or at the rim area of the at least one anchoring member is provided as a partial reinforcement.

According to a variant of the implantable device the first end and/or the second end of the main body has one or multiple slings or loops interlaced with each other and/or located adjacent to each other and/or intertwined with each other. These slings or loops can form a regular rim or an irregular rim. A regular rim is for example built by slings or loops with equal sizes and an irregular rim is built by slings or loops of different sizes, e.g. with two different sizes. Advantageously the arrangement of slings or loops with different sizes is regular, for example one big sling or loop after three small slings or loops. The implantable device can therefore be adapted to the implantation site at the patient. An irregular rim has the advantage that the bigger slings or loops can extend into the papillar muscle of the heart and retain there, whereby an enhanced fixation of the inventive implantable device is achieved.

Preferably the main body of the implantable device is according to a variant in the first operating state (primary form) stent-like. Thereby the inventive implantable device can be implanted in an easy way using a catheter.

In a preferred variant of the inventive implantable device both ends of the wire-like elements are connectable or connected to each other, particularly by using an additional element by twisting, gluing, welding, soldering or another joining technology. Because both ends of the wire-like elements are connectable or connected to each other it is guaranteed that none of both ends injure surrounding vessel or organ after the implantation of the implantable device according to the invention.

In a preferred variant of the inventive implantable device the implantable device has around an oval cross-section in the first operating state (primary form). In the second operating state (secondary form) of the implantable device the implantable device has a round and oval cross-sections in areas where no anchoring members are located, preferably additionally in areas of the at least one anchoring member a round or oval cross-section as well.

Preferably the diameter of the implantable device in the second operating state (secondary form) is in areas outside of the anchoring members about 35 mm. The length of the inventive implantable device in the second operating state (secondary form) is maximum 50 mm.

According to a variant of the inventive implantable device the main body has one or multiple layers. Thereby the stability or the fluid tightness of the main body can be adapted.

According to a further variant of the inventive implantable device the main body and the first membrane element are built integrally. This can be for example achieved thereby that the first end of the main body or the second end of the main body in the second operating state (secondary form) extend inwardly, wherein the first end of the main body respectively the second end of the main body form a valve element in the first opening of the main body respectively the second opening of the main body.

The invention further refers to a main body and a membrane element for an implantable device according to the invention.

In the following the invention will be explained with respect to embodiments shown in the figures.

DETAILED DESCRIPTION

Figure 1:
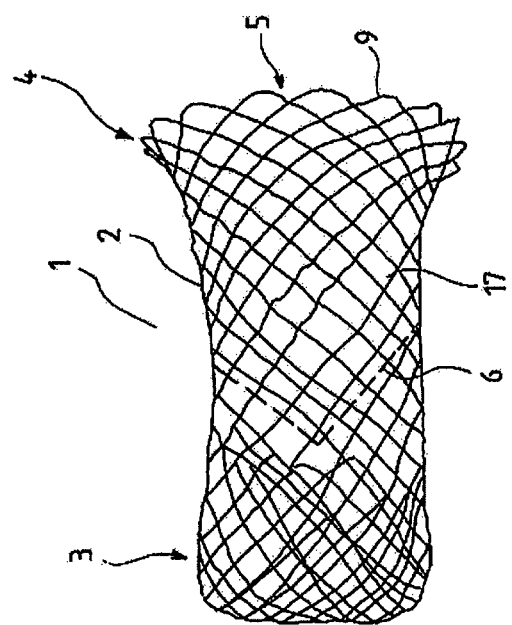
FIG. 1 a perspective view of a $1^{st}$ embodiment of an inventive implantable device, FIG. 2 a sectional view of the $1^{st}$ embodiment of the inventive implantable device from FIG. 1, FIG. 3 alternative embodiments of the implantable device from FIG. 1, FIG. 4 a perspective view of a $2^{nd}$ embodiment of an inventive implantable device, FIG. 5 a top view of the first end of the implantable device from FIG. 4, FIG. 6 a perspective view of a $3^{rd}$ embodiment of an inventive implantable device, FIG. 7 a top view of the first end of the implantable device from FIG. 6, FIG. 8 a perspective view of a $4^{th}$ embodiment of an inventive implantable device, FIG. 9 a top view of the first end of the implantable device from FIG. 8, FIG. 10 a perspective view of a $5^{th}$ embodiment of an inventive implantable device, FIG. 11 a perspective view of a $6^{th}$ embodiment of an inventive implantable device, FIG. 12 a perspective view of a $7^{th}$ embodiment of an inventive implantable device, FIG. 13 a perspective view of an $8^{th}$ embodiment of an inventive implantable device, FIG. 14 a detailed view of a single wire for building a wire element of an inventive implantable device, FIG. 15 a detailed view of a multiple wire for building a wire element of an inventive implantable device, FIG. 16 detailed views of wire strands for building a wire element of an inventive implantable device, FIG. 17 a sectional view of a $9^{th}$ embodiment of an inventive implantable device, FIG. 18 a sectional view of $10^{th}$ embodiment of an inventive implantable device, FIG. 19 a sectional view of an $11^{th}$ embodiment of an inventive implantable device, FIG. 20 a sectional view of a $12^{th}$ embodiment of an inventive implantable device in the implanted state, FIG. 21 a sectional view of the $13^{th}$ embodiment of an inventive implantable device, FIG. 22 a sectional view of a $14^{th}$ embodiment of an inventive implantable device, FIG. 23 a sectional view of a $15^{th}$ embodiment of an inventive implantable device, FIG. 24 a sectional view of a $16^{th}$ embodiment of an inventive implantable device, FIG. 25 a sectional view of a $17^{th}$ embodiment of an inventive implantable device, FIG. 26 a sectional view of an $18^{th}$ embodiment of an inventive implantable device, FIG. 27 a sectional view of a $19^{th}$ embodiment of an inventive implantable device, FIG. 28 a sectional view of a $20^{th}$ embodiment of an inventive implantable device, FIG. 29 a sectional view of a $21^{st}$ embodiment of an inventive implantable device, FIG. 30 a sectional view of a $22^{nd}$ embodiment of an inventive implantable device, FIG. 31 a detailed view of a main body of an inventive implantable device with two layers, FIG. 32 a detailed view of a main body of an inventive implantable device with three layers, FIG. 33 an exemplary implantation process of an inventive implantable device, FIG. 34 a detailed view of a $1^{st}$ embodiment of a rim area of an inventive implantable device, FIG. 35 a detailed view of a $2^{nd}$ embodiment of a rim area of an inventive implantable device, and FIG. 36 a detailed view of a $3^{rd}$ embodiment of a rim area of an inventive implantable device.

In FIG. 1 is shown a perspective view of the first embodiment of an inventive implantable device 1 for use in the human and/or animal body 24 to replace an organ valve. The implantable device 1 comprises a main body 2 having a first end 3 and a second end 4, wherein the first end 3 and the second end 4 each have an opening 5 to provide a fluid connection through the main body 2 between the first end 3 and the second end 4. The main body has in a first operating state (primary form) a large ratio of length to transverse expansion along the longitudinal axis of the main body 2 and in a second operating state (secondary form) a smaller ratio of length to transverse expansion along the longitudinal axis of the main body 2, wherein the implantable device 1 in FIG. 1 is shown in the second operating state (secondary form).

The main body 2 of the implantable device 1 is reversibly transferable from the secondary form to the primary form countered to elastic material forces by the application of a force.

In the centre between the first end 3 of the main body 2 and the second end 4 of the main body 2 the implantable device 1 of FIG. 1 has a first membrane element 6, wherein the membrane element 6 is formed in such a manner that it allows the fluid connection through the main body 2 in a first flow direction and blocks the same in a second flow direction opposite the first flow direction.

The main body 2 of the implantable device 1 of FIG. 1 is formed from a single wire-like element 9 or from a plurality of wire-like elements 9 connected to each other by means of interlocking winding and/or twisting and/or weaving in the manner of a woven and/or layered fabric and/or net.

The implantable device 1 of FIG. 1 is in the second operating state (secondary form) formed stent-like. The first end 3 of the main body 2 of the implantable device 1 of FIG. 1 is in the second operating state (secondary form) folded on each other to a double-layer, wherein the double-layer of the first end 3 is achieved by a backfolding inwardly into the implantable device 1.

Thereby an implantable device 1 to replace an organ valve is created, that due to the double-layer at the first end 3 of the main body 2 offers a particularly good fixation in a vessel and/or organ. Because the main body 2 is reversibly transferable from the primary form into the secondary form it can be transported to the implantation site via a catheter 26 without problems. By pushing out the implantable device 1 out of the catheter 26 the implantable device 1 unfolds from the primary form into the secondary form, wherein the diameter of the main body is enhanced and the length in general is reduced. Because of the possibility to reversibly transfer from the primary into the secondary form and vice versa from the secondary into the primary form the implantable device 1 can be retracted into the catheter 26 in case during the implantation it is recognized that the implantation does not proceed properly, particularly that the implantable device 1 is not orderly placed with respect to coronary arteries and/or the natural heart valve and/or the aorta as well as the heart ventricle. By using a single wire-like element 9 which forms the implantable device 1 by means of interlocking winding and/or twisting and/or weaving in the manner of a woven and/or layered fabric and/or net it is achieved that the inventive implantable device 1 has a high flexibility without the risk that single elements of the implantable device 1 break during the transfer from the primary form into the secondary form or from the secondary form into the primary form. The design of the implantable device 1, particularly of the main body 2, of a single wire-like element has the advantage that no connection points, e.g. welding points, between the single element of the main body are present, which could break easily. Precisely such a break of single elements of an implantable device 1 can result in sharp edge areas protruding out of the device which could injure or perforate a wall, particularly an aorta. The structure of the main body 2 can further be built more regular by a single wire as it is the case when connecting several ring-like elements, as it is known from the prior art. The use of a plurality of wire-like elements 9 has the advantage that the inventive implantable device 1 can be easily built by a machine.

The implantable device 1 of FIG. 1 comprises at least one radio-opaque marker, particularly in the form of a marker tag, marking or marker wire. The radio-opaque marking is particularly located in the area of the main body 2, thereby it is possible to watch the positioning during the implantation particularly with respect to the connection to coronary vessels using a monitor or such a like. Therefore particularly an X-ray display or magnetic resonance imaging is suitable which can display an axial position of the implantable device 1 in the body of the patient, particularly for an aortic valve replacement. The marking can be provided at different positions of the main body 2 or the implantable device 1, particularly in the area of openings in the main body 2.

The implantable device 1 shown in FIG. 1 consists of shape memory material, particularly of nitinol or a plastic with memory shaped effect. According to the application of the implantable device 1 it can be completely or partially consist of an absorbable material, particularly of an absorbable plastic with memory shaped effect.

The first membrane element 6 of the implantable device 1 of FIG. 1 consists of a synthetic or biological material, particularly of polyurethane. The first membrane element 6 is further provided with a coating for establishing a biostability, particularly a titanium coating.

The main body 2 and the first membrane element 6 can be detachable or inseparable connected or connectable to each other, particularly by gluing, welding, sewing, fusing, dip-coating or another joining technology.

The first membrane element 6 is in the second operating state (secondary form) of the implantable device 1 centrically located between the first end 3 of the main body 2 and the second end 4 of the main body 2.

Because the main body 2 is reversibly transferable from the secondary form to the primary form counter to elastic material forces by the application of a force the implantable device 1 according to FIG. 1 is relocatable and explantable.

The implantable device 1 is in the second operating state (secondary form), as shown in FIG. 1, between the first end 3 and the second end 4 of the main body 2 at least partially, preferably completely, deformable in a radial direction, such that the main body 2 can adapt to a vessel wall. Because the main body lays against the vessel wall during the implantation it is achieved that the inventive implantable device after the implantation does not relocate itself, for example caused by the pumping action of the heart. The inventive implantable device 1 of FIG. 1 can be for example introduced via the carotid artery or the axillary artery into the human or animal body 24, which results in comparison to an implantation via the inguinal region of the patient to a shorter implantation path.

In case the main body 2 is built by a single wire-like element 9 this is for example be formed by a single wire 17, a wire strand 18 of at least two single wires or a multiple wire 19. The diameter can be for example round, oval, semi-circled, quadratic or rectangular and also vary over the length of the single wire-like element 9. The wire-like element 9 can if necessary be wrapped with platinum or gold or wolfram or be provided with platinum or gold rings, to enhance the X-ray contrast. In case of a wire strand 18 for example single wires of platinum or gold can be included into the wire strand 18 to enhance the X-ray contrast. Particularly the usage of a wire strand 18 or a multiple wire 19 has the advantage that the implantable device 1 according to the invention is particularly flexible with a good stability.

According to the invention the main body 2 is formed by means of interlocking winding and/or twisting and/or weaving in the manner of a woven and/or layered fabric and/or net. By the interlocking winding and/or twisting and/or weaving of the single wire-like element 9 or the plurality of wire-like elements 9 connected to each other a tube-like or cylindrical element is built in the first operating state (primary form). Both ends of the single wire-like element 9 are for example located at the first end 3 or the second end 4 or in a side surface of the longitudinal main body 2.

As can be further seen from FIG. 1 the implantable device 1 has in the second operating state (secondary form) a round cross-section.

Figure 2:
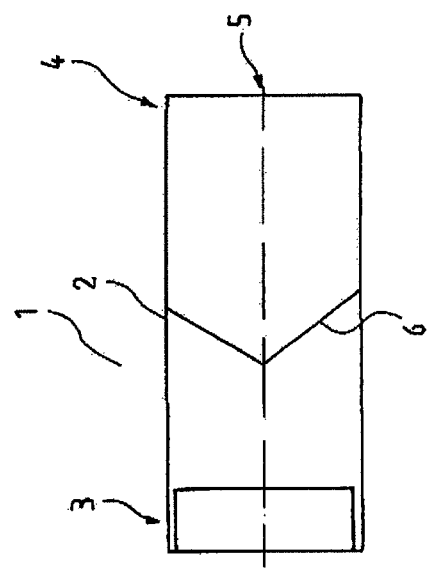

In FIG. 2 a sectional view of the 1$^{st}$ embodiment of the implantable device 1 of FIG. 1 is shown. FIG. 2 particularly shows that at the first end 3 of the main body 2 of the implantable device 1 a double-layer is located, formed by a backfolding inwardly into the implantable device. Because of the double-layer at the first end 3 the anchoring of the implantable device 1 in the second operating state (secondary form) at the implantation site is enhanced.

In FIG. 3a alternative embodiments of the implantable device 1 of FIG. 1 are shown. The shown alternative embodiments differ with respect to the backfolding at the first end 3 and/or the second end 4 of the main body 2 of the implantable device 1.

In FIG. 3b the first end 3 as well as the second end 4 of the main body 2 of the implantable device 1 are double-layered by a backfolding inwardly into the implantable device 1.

In FIG. 3 the first end 3 of the main body 2 of the implantable device 1 is double-layered by a backfolding outwardly onto the main body 2 and the second end 4 of the main body 2 of the implantable device 1 is double-layered by backfolding into the implantable device 1.

According to FIG. 3c the first end 3 of the main body 2 of the implantable device 1 is backfolded inwardly into the implantable device 1, to build a double-layer and the second end 4 is backfolded outwardly onto the main body to build a double-layer.

According to FIG. 3d the first end 3 and the second end 4 of the main body 2 of the implantable device are backfolded outwardly onto the main body 2 to create a double-layer at the first end 3 and the second end 4 of the main body 2 of the implantable device 1.

Figure 4:
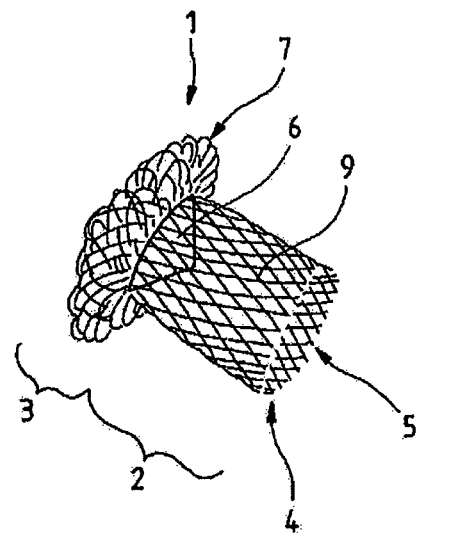

In FIG. 4 a perspective view of the $2^{nd}$ embodiment of an inventive implantable device 1 for use in the human and/or animal body 24 to replace an organ valve is shown. The implantable device 1 comprises a main body 2 having a first end 3 and a second end 4, wherein the first end 3 and the second end 4 each have an opening 5 to provide a fluid connection between the first end 3 and the second end 4 through the main body 2. The main body 2 has in a first operating state (primary form) a large ratio of length to transverse expansion along the longitudinal axis of the main body 2 and in a second operating state (secondary form) a smaller ratio of length to transverse expansion along the longitudinal axis of the main body 2. The implantable device 1 of FIG. 4 is shown in the second operating state (secondary form).

The main body 2 of the implantable device 1 is reversibly transferable from the secondary form to the primary form counter to elastic material forces by the application of a force.

At the first end 3 of the main body 2 of the implantable device 1 of FIG. 4 a first membrane element 6 is located, wherein the membrane element 6 is formed in such a manner that it allows a fluid connection through the main body 2 in a first flow direction and block the same in a second flow direction opposites the first flow direction.

Furthermore the main body 2 of the implantable device 1 of FIG. 4 comprises in the second operating state (secondary form) at the first end 3 a radially outwardly of the main body 2 extending anchoring member 7 for anchoring the device 1 in an organ and/or in a vessel.

The main body 2 of the implantable device 1 of FIG. 4 is formed of a single wire-like element 9 by means of interlocking winding and/or twisting and/or weaving in the manner of a woven and/or layered fabric and/or net.

Thereby an implantable device 1 to replace an organ valve is created which has, because of the radially extending anchoring member 7 at the first end 3 of the main body 2, a particularly good anchoring in a vessel and/or organ. When using the implantable device 1 according to FIG. 4 as a heart valve replacement the first end 3 with the anchoring member 7 can for example extend into the left heart ventricle and anchor there and the second end 4 of the main body 2 can lay against the aorta wall. Because the main body 2 is reversibly transferable from the primary form into the secondary form it can be transported to the implantation site via a catheter 26. When leaving the catheter 26 the implantable device 1 unfolds from the primary form into the secondary form, wherein the diameter of the main body 2 is enhanced and therefore the overall length is reduced. Because of the possibility of the reversible transfer from the primary into the secondary from and vice versa from the secondary into the primary form a retracting of the implantable device 1 into the catheter 26 is possible. In case during the implantation it is recognized that it does not proceed properly, particularly in case the implantable device 1 is not orderly placed with respect to the connections to coronary arteries and/or the natural heart valve and/or the aorta as well as the heart ventricle. Because of the usage of a single wire-like element 9 which forms the implantable device 1 by means of interlocking winding and/or twisting and/or weaving in a manner of a woven and/or layered fabric and/or net the advantage is achieved that the inventive implantable device 1 has a high flexibility without the risk that single elements of the implantable device 1 break by a transfer from the primary form into the secondary form or from the secondary form into the primary form. Forming the implantable device 1, particularly the main body 2, from a single wire-like element 9 has the further advantage that no connecting points, e.g. welding points, between single elements of the main body 2 are present, which could break easily. Such a breakage of single elements of an implantable device 1 can result in sharp edged areas which protrude out of the device, and could injure or perforate the wall, particularly the aorta. The structure of the main body 2 can be built smoother by an integral design as it is possible by connecting single ring-like elements as known from the prior art.

The radially outwardly of the main body 2 extending anchoring member 7 is circumferentially provided at the circumference of the main body 2 at the first end 3 of the main body 2.

The implantable device 1 of FIG. 4 comprises at least one radio-opaque marker, not shown, particularly in the form of a marker tag, marking or marker wire. The radio-opaque marker is located particularly in the area of the main body 2. Thereby it is possible to check the positioning during the implantation, particularly with respect to the connections to coronary vessels using a monitor or such a like. Therefore particularly X-ray imaging or magnetic resonance imaging is suitable which can display an axial positioning of the implantable device 1 in the body of the patient, which is necessary for an aortic valve replacement. The marker can be provided at different areas of the main body 2 or the implantable device 1, particularly in the areas of openings in the main body 2.

The implantable device 1 shown in FIG. 4 consists of a shape memory material, particularly of nitinol or a plastic with memory shape effect. Depending on the application of the implantable device 1 it can be completely or partially consist of an absorbable material, particularly of an absorbable plastic with memory shaped effect.

The first membrane element 6 of the implantable device 1 of FIG. 4 consists of a synthetic or biological material, particularly of polyurethane. The first membrane element 6 is further provided with a coating for establishing a biostability, particularly with a titanium coating.

The main body 2 and the first membrane element 6 are detachable or inseparable connected or connectable to each other, particularly by gluing, welding, sewing, fusing, dip-coating or another joining technology.

The first membrane element 6 is in the second operating state (secondary form) of the implantable device 1 located at the first end 3 of the main body 2.

The main body 2 is reversibly transferable from the secondary form into the primary form counter to elastic material forces by application of a force the implantable device 1 of FIG. 4 is relocatable or explantable.

The implantable device 1 is in the second operating state (secondary form) as shown in FIG. 4, between the first end 3 and the second end 4 of the main body 2 at least partially, preferably completely, deformable in a radial direction, such that the main body 2 can adapt to a vessel wall and/or circumference of an opening and/or edge of an defect organ valve. Because that the main body 2 can adapt during the implantation to a vessel wall and/or circumference of an opening and/or edge of a defect organ valve it is achieved that the inventive implantable device 1 does not relocate itself for example caused by a pumping action of the heart.

For instance the inventive implantable device 1 is introduced during the implantation into the human and/or animal body 24 as far as the location of the heart valve, particularly the aortic valve, such that the natural valve during the transfer of the inventive implantable device 1 from the first operating state (primary form) into the second operating state (secondary form) is pushed against the vessel wall and fixed there by the implantable device 1. In general it is even possible to introduce a further implantable device 1 into an already implanted device 1, wherein the first membrane element 6 of the first implanted device 1 is also pushed against the wall of the main body 2. Such an insertion of a further implantable device 1 into an already implanted device 1 can be for example necessary in case of a reduced stability and flexibility of the first membrane element 6. In general it is also possible to introduce an implantable device 1 according to FIG. 4 with a membrane element 6 as a valve replacement where prior to the implantation the old natural valve has been removed, particularly by a surgery. Particularly in case of a strong calcification of the natural heart valve it can be advantageous to completely remove it because it is in general inflexible. In such a case it would be hardly possible to push the natural valve onto the vessel wall. Furthermore there would remain a constriction in this area, which is undesirable because it would result in a reduced flow-crossed section and lead to an increased pressure and therefore to disadvantageous for the patients. In case of a heart valve insufficiency the implantable device 1 can alternatively be implanted into the insufficient valve, particularly the aortic valve or mitral valve, without removing the natural valve before.

The inventive implantable device 1 of FIG. 4 is for example introduced via the carotid aorta or the arteria axillaris into the human or animal body 24 which results in comparison to an implantation via the inguinal region of the patient to a reduced implantation path.

The main body 2 of the implantable device 1 of FIG. 4 is particularly arranged such that the projecting anchoring member 7 at the first end 3 protrudes into the heart ventricle, for example into the left heart ventricle, and the remaining area of the main body 2 anchors to a vessel wall, for example the aorta wall. Thereby a particular good anchoring and firm arrangement is achieved. The dimensions of the anchoring member 7 and the main body 2 can be individually adapted to a patient according to the anatomy of the particular patient. Also the dimension of the projecting of the anchoring member 7 can be chosen individually. However, in general a standardization is possible according to which the anchoring member 7 protrudes in such a way and in such dimensions that the majority of patients can be provided with such a kind of main body 2 or implantable device 1.

The single wire-like element 9 of the inventive implantable device 1 consists of a single wire 17, a wire strand 18 of at least two single wires or a multiple wire 19. The cross-section can be for example round, oval, semi-circled, quadratic or rectangular and also vary over the length of the single wire-like element 9. The single wire-like element 9 can be if necessary wrapped with platinum or gold or wolfram or be provided with platinum or gold rings, to enhance the X-ray contrast. In case of a wire strand 18 particularly single wires of platinum or gold can be integrated into the wire strand 18 to enhance the X-ray contrast. Particularly the usage of a wire strand 18 or a multiple wire 19 has the advantage that the implantable device 1 according to the invention is particularly flexible with a sufficient stability.

According to the invention the main body 2 is formed by means of interlocking winding and/or twisting and/or weaving in the manner of a woven and/or layered fabric and/or net. By the interlocking winding and/or twisting and/or weaving of the single wire-like element 9 in the first operating state (primary form) a generally tube-like or cylindrical element is achieved. The both ends of the single wire-like element 9 are located at the first end 3 or the second end 4 or in a side wall of the longitudinal main body 2. Thereby on the one hand the risk of injuries for the patient in which the implantable device 1 is implanted is reduced and on the other hand the stability of the main body 2 is enhanced.

The anchoring member 7 of the implantable device 1 is in the second operating state (secondary form) disc-shaped, as shown in FIG. 4. After the implantation of the inventive implantable device 1 the disc-shaped anchoring member 7 rests for example against the inner wall of the heart and the remaining cylindrical part of the main body 2 extends through an opening, which should be provided with a valve device by the implantable device 1, into a vessel, so that the disc-shaped anchoring member 7 can conform to the inner wall of the heart it is partially be built deformable.

The anchoring member 7 has in the second operating state (secondary form) of the main body 2 a first sub-portion 22 and a second sub-portion 23, wherein the first sub-portion 22 extends in a radial direction of the main body 2 outwardly and the second sub-portion 23 is folded backwards in a radial direction of the main body 2 inwardly, particularly in such a way, that the first sub-portion 22 and the second sub-portion 23 are folded onto another to a double-layer. The backfolding of the anchoring member 7 is located towards the middle of the main body 2. The anchoring member 7 is due to the backfolding and the resulting double-layer in this area at least partially deformable, such that the anchoring member 7 can better conform to an organ or vessel wall.

The first end 3 and the second end 4 of the main body 2 have one or more multiple slings or loops interlaced with each other and/or located adjacent to each other and/or intertwined with each other. These slings or loops 21 form a regular rim 28. The regular rim 28 is for example be formed by slings or loops 21 with the same size.

Both ends of the wire-like elements 9 are connectable or connected to each other, particularly by using an additional element, by twisting, gluing, welding, foldering or another joining technology. Thereby it is guaranteed that none of both ends can injure a neighbouring vessel or organ after the implantation of the implantable device 1.

As can be further seen from FIG. 4 the implantable device 1 has in the second operating state (secondary form) at least in the area where no anchoring member 7 is located a round cross-section. The implantable device 1 of FIG. 4 has also in the area of anchoring member 7 a round cross-section.

Figure 5:
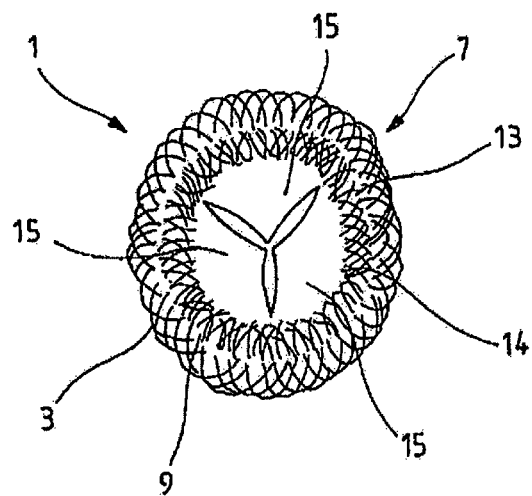

In FIG. 5 a top view onto the first end 3 of the implantable device 1 of FIG. 1 is shown. It can be particularly seen from FIG. 5 that the first membrane element 6 has a ring portion 13 and a valve portion 14 connected to the ring portion 13. The valve portion 14 is provided with three leaflet elements 15.

The first membrane element 6 is in the second operating state (secondary form) located at the first end 3 of the main body 2. The first membrane element 6 is for example in the area of the ring portion 13 connected to the first end 3 of the main body 2, for example by sewing. The valve portion 14 is dimensioned such that the fluid connection through the main body 2 in a first flow direction is allowed and in a second flow direction opposite to the first flow direction is blocked, particularly in such a way that the cross-section of the valve portion 14 in the cross-section corresponds to the cross-section of the valve arrangement to be replaced.

Figure 6:
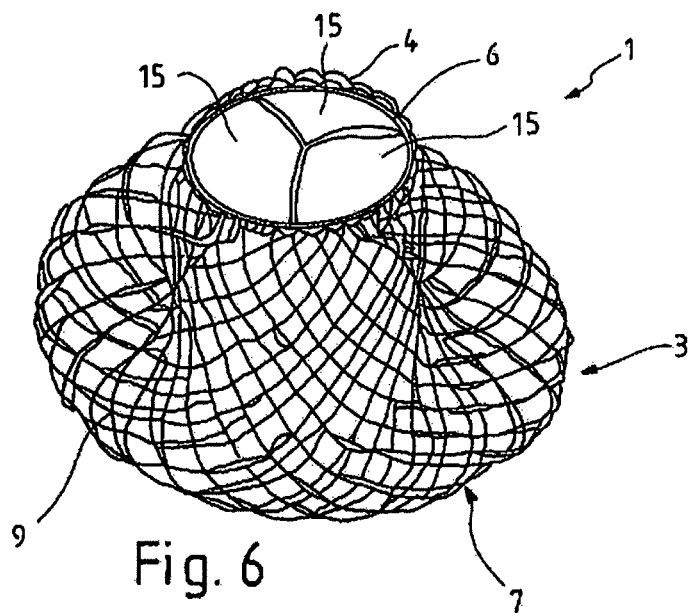

FIG. 6 shows a perspective view of a third embodiment of an inventive implantable device 1. The implantable device 1 for use in the human and/or animal body 24 to replace an organ valve according to FIG. 6 comprises a main body 2 having a first end 3 and a second end 4, wherein the first end 3 and the second end 4 each have an opening 5 to provide a fluid connection between the first end 3 and the second end 4 through the main body 2 and a first membrane element 6 arranged at the second end 4 of the main body 2, wherein the membrane element 6 is formed in such a manner that it allows the fluid connection through the main body 2 in a first flow direction and blocks the same flow in a second flow direction opposites the first flow direction. The main body 2 has in a first operating state (primary form) a large ration of length to transverse expansion along the longitudinal axis of the main body 2 and in a second operating state (secondary form) a smaller ratio of length to transverse expansion along the longitudinal axis of the main body 2. The main body 2 is reversibly transferable from the secondary form to the primary form counter to elastic material forces by the application of a force. The implantable device 1 in FIG. 6 is shown in the second operating state (secondary form).

The main body 2 has in the second operating state (secondary form) at the first end 3 a radially outwardly of the main body 2 protruding anchoring member 7 for anchoring the device in an organ and/or in a vessel.

The main body 2 of the implantable device 1 from FIG. 6 is formed from a single wire-like element 9 or from a plurality of wire-like elements 9 connected to each other by means of interlocking winding and/or twisting and/or weaving in the manner of a woven and/or layered fabric and/or net.

The embodiment according to FIG. 6 differs from the embodiments according to FIG. 5 thereby that the first membrane element is located at the second end 4 of the main body 2. Furthermore the first membrane element 6 according to the embodiment of FIG. 6 differs from the embodiment from FIG. 5 thereby that it consists of three leaflet elements 15 and has no ring portion 13 as the first membrane element 6 from FIG. 5.

Figure 7:
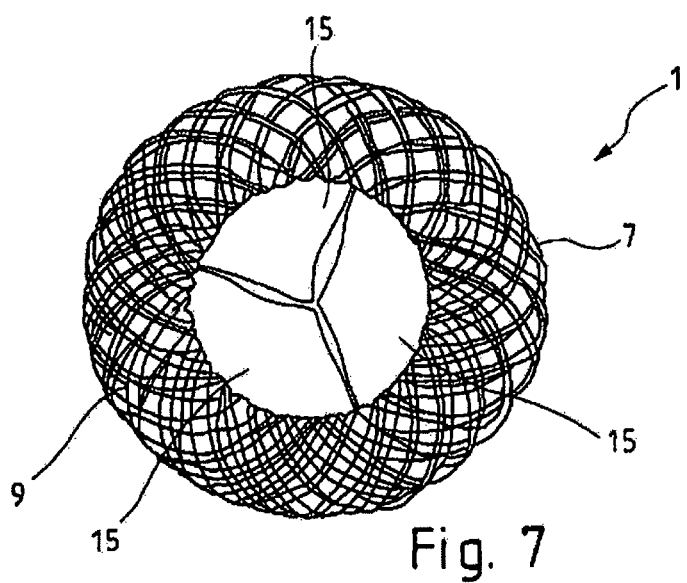

In FIG. 7 a top view onto the first end 3 of the implantable device 1 from FIG. 6 is shown. The first membrane element 6 of the embodiment of FIG. 7 is located at the end of the implantable device 1 extending into the plane of projection and visible by the fluid connection in the longitudinal direction through the main body 2. The remaining design of the embodiment according to FIGS. 6 and 7 correspond to the embodiment according to FIGS. 4 and 5.

Figure 8:
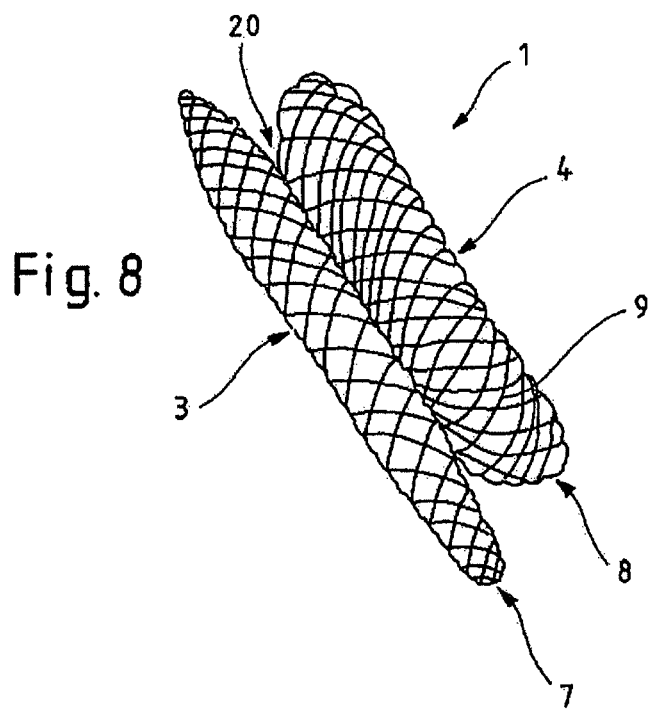

In FIG. 8 is shown a perspective view of a 4$^{th}$ embodiment of an inventive implantable device. The implantable device 1 comprises a main body 2 having a first end 3 and a second end 4, wherein the first end 3 and the second end 4 each have an opening 5 to provide a fluid connection between the first end 3 and the second end 4 through the main body 2 and a first membrane element arranged inside the main body 2, wherein the membrane element 6 is formed in such a manner that it allows the fluid connection through the main body 2 in a first flow direction and blocks the same in a second flow direction opposite the first flow direction. The main body 2 has in a first operating state (primary form) a large ratio of length to transverse expansion along the longitudinal axis of the main body 2 and in a second operating state (secondary form) a smaller ratio of length to transverse expansion along the longitudinal axis of the main body 2, wherein the main body 2 of the implantable device 1 in FIG. 8 is shown in the second operation state (secondary form). The main body 2 is reversibly transferable from the secondary form to the primary form counter to elastic material forces by the application of a force.

The main body 2 has in the second operating state (secondary form) at the first end 3 and at the second end 4 radially outwardly of the main body 2 extending anchoring members 7, 8 for anchoring the device in an organ and/or in a vessel.

The main body 2 is formed from a single wire-like element 9 or from a plurality of wire-like elements 9 connected to each other by means of interlocking winding and/or twisting and/or weaving in the manner of a woven and/or layered fabric and/or net.

The two radially outwardly of the main body 2 extending anchoring members 7, 8 are circumferentially provided at the circumference of the main body 2 at the first end 3 and the second end 4 of the main body 2.

Furthermore the implantable device 1 of FIG. 8 comprises at least one radio-opaque marker, particularly in the form of a marker tag, marking or marker wire.

The implantable device 1 of FIG. 8 consists completely or partially of a shape memory material, particularly of nitinol or a plastic with memory shape effect. Particularly when using a plastic with memory shape effect the implantable device 1 can be completely or partially built absorbable.

Because the main body 2 of the implantable device 1 according to FIG. 8 is reversibly transferable from the secondary form into the primary form counter to elastic material forces by applying a force the implantable device 1 is relocatable and/or explantable.

Furthermore the implantable device 1 is in the second operating state (secondary form) between the first end 3 and the second end 4 of the main body 2 at least partially, preferably completely, deformable in a radial direction, such that the main body 2 can adapt to a vessel wall and/or circumference of an opening and/or edge of a defect organ valve.

The single wire-like element 9 of the implantable device 1 of FIG. 8 consists of a single wire 17, a wire strand 18 of at least two single wires or a multiple wire 19. The both ends of the wire-like element 9 are located at the first end 3 or the second end 4 or in a side surface of the main body 2.

The first anchoring member 7 is located at the first end 3 of the main body 2 and the second anchoring member 8 is located at the second end 4 of the main body 2. The first anchoring member 7 and the second anchoring member 8 are disc-shaped in the second operating state (secondary form). The first anchoring member 7 is flat and the second anchoring member 8 is bulgy. Between the first anchoring member 7 and the second anchoring member 8 the main body 2 of the implantable device 1 comprises an intermediate member 20, which has a smaller diameter as the first anchoring member 7 and the second anchoring member 8. The diameters of the two anchoring members 7, 8 are different. As can be seen from FIG. 8 the diameter of the first anchoring member 7 is larger than the diameter of the second anchoring member 8.

The two anchoring members 7, 8 have in the second operating state (secondary form) of the main body each a first sub-portion 22 and a second sub-portion 23, wherein the first sub-portion 22 extends in a radial direction of the main body 2 outwardly and the second sub-portion is folded back in a radial direction of the main body 2 inwardly, particularly in such a way, that the first sub-portion 22 and the second sub-portion 23 are folded onto another to a double-layer. The bulgy design of the second anchoring member 8 according to FIG. 8 also forms a double-layer folded anchoring member 8 in the sense of the invention.

The first end 3 and the second end 4 of the main body 2 of the implantable device 1 according to FIG. 8 each have one or multiple slings or loops 21 interlaced with each other and/or located adjacent to each other and/or intertwined with each other. The slings or loops 21 form a regular rim 28.

Both ends of the wire-like elements 9 are connectable or connected to each other, particularly by using an additional element, by twisting, gluing, welding, soldering, or another joining technology.

The cross-section of the implantable device 1 of FIG. 8 is in the first operating state (primary form) round or oval. In the second operating state (secondary form) the implantable device 1 has a cross-section in areas where no anchoring member 7, 8 is located which is round or oval. In areas of the anchoring members 7, 8 the implantable device 1 of FIG. 8 also has a round or oval cross-section.

The diameter of the implantable device 1 of FIG. 8 in the second operating state (secondary form) in areas outside of the anchoring members 7, 8 particularly in the area of the intermediate member 20 is about 35 mm. The length of the implantable device 1 in the second operating state (secondary form) is maximal 50 mm.

The main body 2 of the implantable device 1 can have one or multiple layers.

Figure 9:
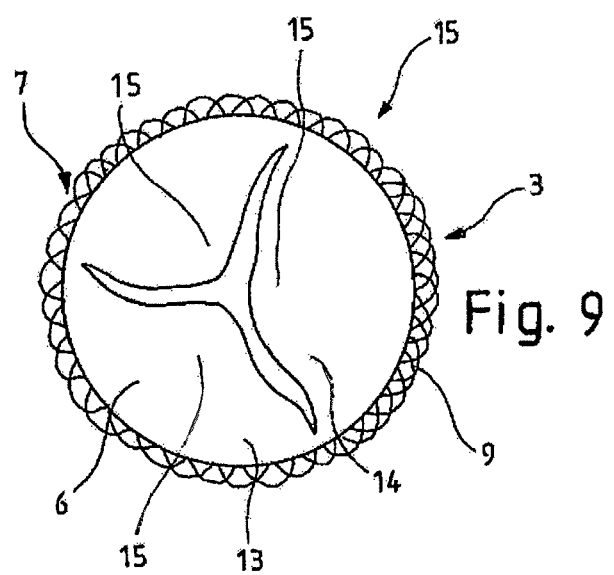

FIG. 9 shows a top view onto the first end of the implantable device of FIG. 8. As can be seen from FIG. 9 at the first end 3 of the main body 2 of the implantable device 1 the first membrane element 6 is located. The first membrane element 6 consists of a synthetic or biological material, particularly of polyurethane. Furthermore the first membrane element 6 comprises a coating for establishing a biostability, particularly by titanium coating.

The main body 2 of the implantable device 1 and the first membrane element 6 are detachable or inseparable connected or connectable to each other, particularly by gluing, welding, sewing, fusing, dip-coating or another joining technology.

The first membrane element 6 has a ring portion 13 and connected to this a valve portion 14. The valve portion 14 of the first membrane element 6 comprises, according to FIG. 9, three leaflet elements 15.

The 4$^{th}$ embodiment of the inventive implantable device shown 1 in FIGS. 8 and 9 with a first anchoring member 7, the second anchoring member 8 and the intermediate member 20 located there between is particularly suitable to replace a bicuspid valve or tricuspid valve. The implantable device 1 according to the 4$^{th}$ embodiment of FIGS. 8 and 9 is located in such a manner in the human or animal body 24, that parts of the papillary muscle of the heart are located in the area of the intermediate member 20 and the first anchoring member 7 and the second anchoring member 8 are located on different sides of the papillary muscle and lay against the papillary muscle, whereby the implantable device 1 is fixed in the heart of the human or animal body 24. In case of a stenosis of the natural valve the old natural valve should be removed, particularly by a surgery and at this place the implantable device 1 with the first membrane element 6 should be implanted as a valve replacement. Particularly in case of a strong calcification of the natural heart valve it is advantageous to completely remove the natural heart valve because it is generally substantially inflexible. In such a case it would be hardly possible to push the natural valve to the vessel wall. Furthermore, there would remain a narrowing in this area which is also not desired because it results in a reduction of the flow cross-section and results in a higher pressure which causes health disadvantages for the patient. In case of a heart valve insufficiency the inventive implantable device 1 can be implanted in the insufficient valve, for example the bicuspid valve (mitral valve) without a prior removal of the natural valve.

Figure 10:
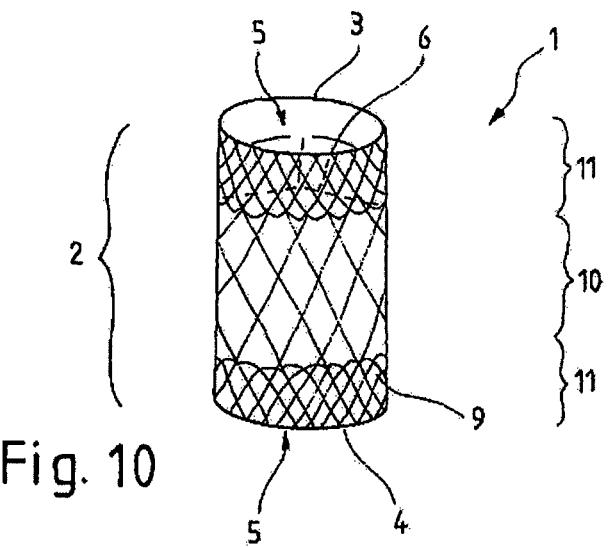

In FIG. 10 a perspective view of a 5$^{th}$ embodiment of an inventive implantable device 1 is shown. The implantable device 1 for use in the human and/or animal body 24 to replace an organ valve comprises a main body 2 having a first end 3 and a second end 4, wherein the first end 3 and the second end 4 each have an opening 5 to provide a fluid connection through the main body 2 between the first end 3 and the second end 4 and a first membrane element 6 arranged inside or at one end of the main body 2, wherein the membrane element 6 is formed in such a manner that it allows the fluid connection through the main body 2 in a first flow direction and blocks the same in a second flow direction opposite the first flow direction. The main body 2 has in a first operating state (primary form) a large ratio of length to transverse expansion along the longitudinal axis of the main body 2 and in a second operating state (secondary form) a smaller ratio of length to transverse expansion along the longitudinal axis of the main body 2. The main body 2 of the implantable device 1 in FIG. 1 is shown in the first operating state (primary form).

The main body 2 of the implantable device 1 is reversibly transferable from the secondary form to the primary form counter to elastic material forces by the application of a force.

In the second operating state (secondary form) the main body 2 has at the first end 3 and/or the second end 4 at least one radially outwardly of the main body 2 extending anchoring member 7, 8 for anchoring the device 1 in an organ and/or in a vessel.

The main body 2 of the implantable device 1 is formed from a single wire-like element 9 or from a plurality of wire-like elements 9 connected to each other by means of interlocking winding and/or twisting and/or weaving in the manner of a woven and/or layered fabric and/or net.

The implantable device 1 of FIG. 10 has areas of different rigidity 10, 11. The areas of different rigidity 10, 11 are formed by differently interlocking winding and/or twisting and/or weaving. In the 5$^{th}$ embodiment of the inventive implantable device 1 of FIG. 10 an area with lesser rigidity 10 is located between areas with higher rigidity 11. The area with lesser rigidity 10 is located at the main body 2 outside of the at least one anchoring member 7, 8. In case the at least one anchoring member 7, 8 is located at the first end 3 and/or second end 4 of the main body 2 the area with lesser rigidity 10 of the main body 2 is located in the intermediate area of the main body 2.

The area with lesser rigidity 10 of the implantable device 1 according to the 5$^{th}$ embodiment of the inventive implantable device 1 of FIG. 10 is built by differently interweaving the single wire-like element 9 of the main body or the plurality wire-like elements 9 of the main body 2 connected to each other. As can be seen from FIG. 10 the mash size in the area of lesser rigidity 10 of the woven and/or layered fabric and/or net formed by means of interlocking winding and/or twisting and/or weaving is larger as in areas with higher rigidity 11.

Figure 11:
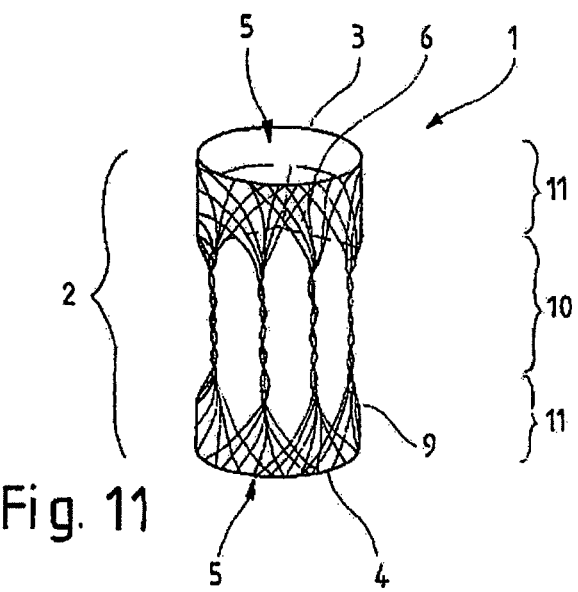

Alternatively the area of lesser rigidity 10 can be for example created by a further interlocking winding and/or twisting of a single wire-like element 9 or the plurality of wire-like elements 9 connected to each other as can be for example seen in the 6$^{th}$ embodiment of the inventive implantable device 1 of FIG. 11.

The implantable device 1 according to the 5$^{th}$ embodiment of FIG. 10 and according to the 6$^{th}$ embodiment of FIG. 11 is in the first operating state (primary form) formed stent-like. A cross-section of the implantable device 1 in the first operating state (primary form) is round or oval.

The areas of different rigidity 10, 11 disclosed with respect of the 5$^{th}$ and 6$^{th}$ embodiment of the implantable device 1 can be combined with the embodiments two to four of the implantable device 1 from FIG. 4 to 9 and the following disclosed embodiments. For example the implantable device 1 according to the 5$^{th}$ and 6$^{th}$ embodiment of FIGS. 10 and 11 can be built in the second operating state (secondary form) according to one of the embodiments two to four from FIGS. 4 to 9.

Figure 12:
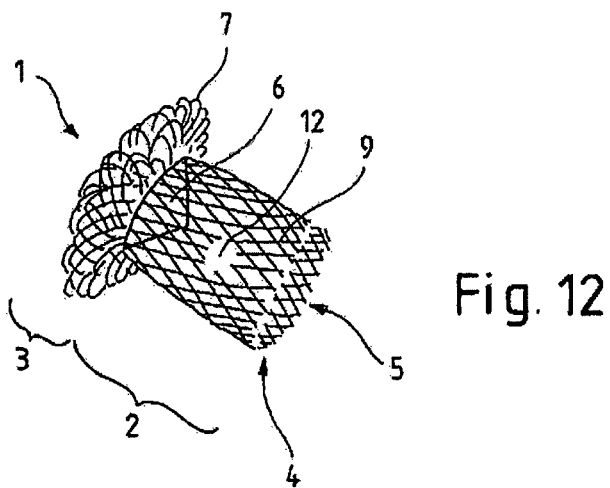

FIG. 12 shows a perspective view of a 7$^{th}$ embodiment of an inventive implantable device 1. The 7$^{th}$ embodiment of the inventive implantable device 1 differs from the second embodiment of the inventive implantable device 1 in that the main body has at least one opening 12 in its circumferential wall, to provide a fluid connection between the inner of the main body 2 and a vessel of the human and/or animal body 24. The at least one opening 12 has a diameter corresponding to a coronary artery. In the 7$^{th}$ embodiment according to FIG. 12 the main body 2 has two openings in its circumferential wall, which in the implanted state of the device 1 are arranged in such a way, that the two openings overlap with coronary arteries. The two openings 12 in the circumferential wall of the main body 2 are located outside of the at least one anchoring member 7, 8.

Figure 13:
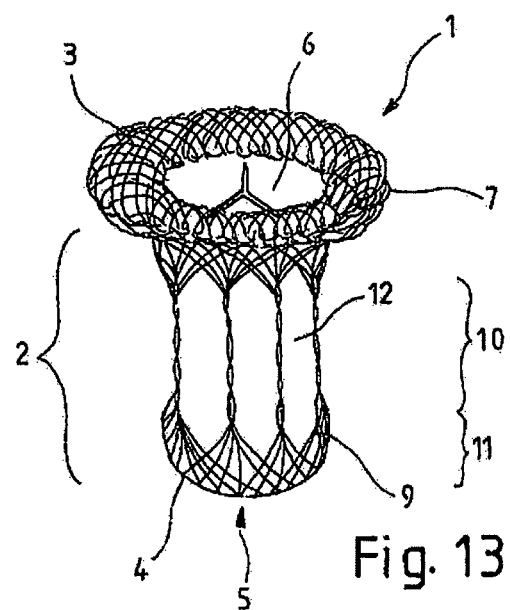

In FIG. 13 a perspective view of an 8$^{th}$ embodiment of the inventive implantable device 1 is shown. The 8$^{th}$ embodiment of the inventive implantable device 1 according to FIG. 13 differs from the 7$^{th}$ embodiment of the inventive implantable device 1 according to FIG. 12 in that the at least one opening in the circumferential wall of the main body 2 is built by a further interlocking winding and/or twisting and/or weaving of the single wire-like element 9 of the main body 2 or a plurality of wire-like elements 9 connected to each other of the main body 2, wherein in the area of the at least one opening 12 in the circumferential wall of the main body 2 a larger mash size is achieved by the further interlocking winding and/or twisting and/or weaving of the single wire-like element 9 of the main body 2 or the plurality of wire-like elements 9 connected to each other of the main body 2 in comparison to the remaining areas of the circumferential wall of the main body 2. In the embodiment according to FIG. 13 the at least one opening 12 in the circumferential wall of the main body 2 is built by a further twisting of the single wire-like element 9 of the main body 2 or the plurality of wire-like elements 9 connected to each other of the main body 2.

The embodiments according to FIGS. 12 and 13 can also be combined with the 3$^{rd}$ to 6$^{th}$ embodiment of the inventive implantable device 1 according to FIGS. 6 to 11 and the following disclosed embodiments.

According to a particularly preferred embodiment at least one radio-opaque marker is located in the area of the at least one opening 12 in the circumferential wall of the main body 2, particularly in the form of a marker tag, marking or marker wire. Thereby the positioning of the implantable device 1 during the implantation of the implantable device 1, for example with respect to the coronary arteries, can be monitored.

Figure 14:
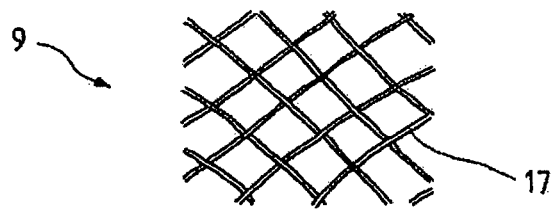
Figure 15:
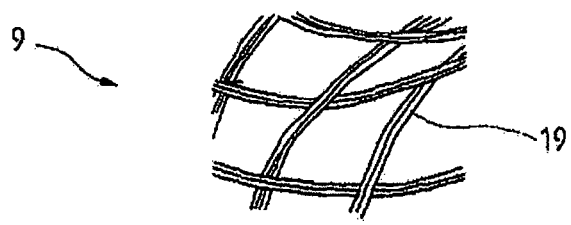
Figure 16:
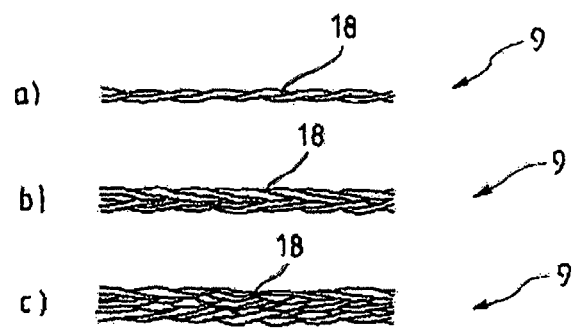

In FIGS. 14 to 16 different designs of the single wire-like element 9 of the main body 2 according to the inventive implantable device 1 are shown. Using a single wire-like element 9 the main body 2 of the implantable device 1 is formed by means of interlocking winding and/or twisting and/or weaving in the manner of a woven and/or layered fabric and/or net.

According to an embodiment the single wire-like element 9 is formed from a single wire 17, as shown in FIG. 14. In FIG. 15 an embodiment is shown according to which the single wire-like element 9 is formed from a multiple wire. In FIG. 16a to 16c wire strands are shown, which form the single wire-like element 9 of the implantable device 1. The wire strand 18 of FIG. 16a consists of two single wires, the wire strand 18 of FIG. 16b consists of four single wires and the wire strand 18 of FIG. 16c consists of six single wires.

The difference between the multiple wire 19 according to FIG. 15 and a wire strand 18 according to FIG. 16 is that the single wires of the wire strands are twisted with each other while the single wires of the multiple wire run parallel to each other.

Advantageously a single wire of the multiple wire 19 according to FIG. 15 or the wire strand 18 according to FIG. 16 is built as a marker wire, to provide a radio-opaque marking within the implantable device 1.

The single wires according to FIGS. 14 to 16 consist completely or partially of a shape memory material, particularly of nitinol or a plastic with memory shaped effect. Particularly when using a plastic with memory shaped effect it can be completely or partially absorbable.

Both ends of the wire-like element 9, as for example shown in FIGS. 14 to 16, are located at the first end 3 or the second end 4 or in a side surface of the main body 2 of the implantable device 1.

The both ends of the wire-like element 9 are advantageously connectable or connected to each other, particularly by using an additional element, by twisting, gluing, welding, soldering or another joining technology.

Figure 17:
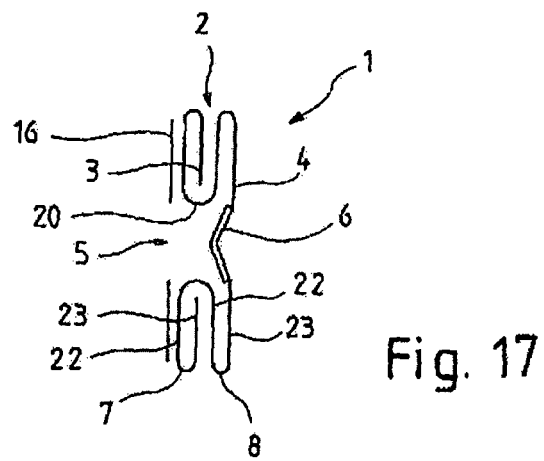

In FIG. 17 a sectional view of a 9$^{th}$ embodiment of an inventive implantable device 1 for the use in the human and/or animal body 24 to replace an organ valve is shown. The implantable device 1 comprises a main body 2 having a first end 3 and a second end 4, wherein the first end 3 and the second end 4 each have an opening 5 to provide a fluid connection through the main body 2 between the first end 3 and the second end 4, and a first membrane element 6 arranged at the second end 4 of the main body 2, wherein the membrane element 6 is formed in such a manner that it allows the fluid connection through the main body 2 in a first flow direction and blocks the same in a second flow direction opposite the first flow direction. The main body 2 has in the first operating state (primary form) a large ratio of length to transverse expansion along the longitudinal axis of the main body 2 and in a second operating state (secondary form) a smaller ratio of length to transverse expansion along the longitudinal axis of the main body 2, wherein the implantable device 1 of FIG. 17 is shown in the second operating state (secondary form) of the main body 2. The main body 2 can be reversibly transferred from the secondary form to the primary form counter to elastic material forces by the application of a force.

In the second operating state (secondary form) the main body 2 has at the first end 3 and the second end 4 an anchoring member 7, 8 for anchoring the device in an organ and/or in a vessel. According to the embodiment of FIG. 17 the first anchoring member 7 is located at the first end 3 of the main body 2 and the second anchoring member 8 is located at the second end 4 of the main body 2.

The main body 2 is formed from a single wire-like element 9 or from a plurality of wire-like elements 9 connected to each other by means of interlocking winding and/or twisting and/or weaving in the manner of a woven and/or layered fabric and/or net.

The regularly outwardly of the main body 2 extending anchoring members 7, 8 are circumferentially provided at the circumference of the main body 2 at the first end 3 and the second end 4.

The implantable device 1 of FIG. 17 can have areas of different rigidity 10, 11, particularly as disclosed with respect to FIGS. 10 and 11. The areas of different rigidity 10, 11 are for example formed by differently interlocking winding and/or twisting and/or weaving. Advantageously an area with lesser rigidity 10 is located between areas with higher rigidity 11 and the area with lesser rigidity 10 is located at the main body 2 outside of the anchoring members 7, 8.

As disclosed with respect to FIGS. 12 and 13 the main body 2 can have in its circumferential wall at least one opening 12 to provide a fluid connection between the inner of the main body 2 and a vessel of the human and/or animal body 24. The at least one opening 12 has advantageously a diameter corresponding to a coronary artery. Particularly the main body 2 has in its circumferential wall two openings 12, which in the implanted state of the implantable device 1 are arranged in such a way, that the two openings 12 overlap the connections to the coronary arteries. Advantageously the at least one opening 12 in the circumferential wall of the main body 2 is located outside of the anchoring member 7, 8.

The at least one opening 12 in the circumferential wall of the main body 2 is for example be built by a further interlocking winding and/or twisting and/or weaving of the single wire-like element 9 of the main body 2 or of the plurality of wire-like elements 9 connected to each other of the main body 2, wherein by the further interlocking winding and/or twisting and/or weaving of the single wire-like element 9 of the main body 2 or of the plurality of wire-like elements 9 connected to each other of the main body 2 a wider mesh size is achieved as in the remaining areas of the circumferential wall of the main body 2.

As already explained with respect to the previous embodiments the implantable device 1 comprises at least one radio-opaque marker, particularly in the form a marker tag, marking or marker wire. Advantageously the at least one radio-opaque marking is located in the area of the opening 12 in the circumferential wall of the main body 2, to check during the implantation whether the opening 12 corresponds with a coronary artery.

The implantable device 1, particularly the main body 2, according to the $9^{th}$ embodiment of FIG. 17 is built completely or partially of a memory-shaped material, particularly of nitinol or a plastic with memory-shape effect. Furthermore the implantable device 1 can consist completely or partially of an absorbable material.

The first membrane element 6 of the implantable device 1 consists of a synthetic or biological material, particularly of polyurethane. Particularly the first membrane element 6 has a coating for establishing a biostability, particularly a titanium coating.

The main body 2 and the first membrane element 6 are detachable or inseparable connected or connectable to each other, particularly by gluing, welding, sewing, fusing, dip-coating or another joining technology.

The first membrane element 6 can have a ring portion 13 and a valve portion 14 connected thereto, as for example disclosed with respect to the second embodiment of the inventive implantable device 1 and shown in FIG. 5. The valve portion 14 comprises advantageously three leaflet elements 15.

According to the embodiment of FIG. 17 the first membrane element 6 is located in the second operating state (secondary form) at the second end 4 of the main body 2.

The implantable device according to the $9^{th}$ embodiment of FIG. 17 comprises a second membrane element 16 to partially close the openings 5 at the first end 3 and the second end 4 for fluids. In the embodiment according to FIG. 17 the second membrane element 16 is located in the second operating state (secondary form) of the main body 2 at the first end 3.

The implantable device 1 of FIG. 17 is relocatable and/or explantable.

The shown implantable device 1 is in the second operating state (secondary form) between the first end 3 and the second end 4 of the main body 2 at least partially, preferably completely, deformable in a radial direction, such that the main body 2 can adapt to a vessel wall and/or circumference of an opening and/or edge of a defect organ valve. The implantable device 1 of FIG. 17 is therefore particularly in the area of the intermediate member 20 between the first anchoring member 7 and the second anchoring member 8 in a radial direction deformable.

As illustrated with respect to FIGS. 14 to 16 the single wire-like element 9 can consist of a single wire 17, a wire strand 18 of at least two single wires or a multiple wire 19.

The both ends of the wire-like element 9 are preferably located at the first end 3 or the second end 4 or a side surface of the main body 2. Advantageously the both ends of the wire-like element 9 are connectable or connected to each other, particularly by using an additional element, by twisting, gluing, welding, soldering or another joining technology.

The first anchoring member 7 and the second anchoring member 8 of the $8^{th}$ embodiment according to FIG. 17 are in the second operating state (secondary form) disc-shaped.

The diameter of the two anchoring members 7, 8 are equal.

The first anchoring member 7 and the second anchoring member 8 each have in the second operating state (secondary form) of the main body 2 a first sub-portion 22 and a second sub-portion 23, wherein the first sub-portion 22 extends in a radial direction of the main body 2 outwardly and the second sub-portion is folded backwards in a radial direction of the main body 2 inwardly, particularly in such a way, that the first sub-portion 22 and the second sub-portion 23 are folded onto another to a double-layer. The backfolding of the first anchoring member 7 of FIG. 17 is directed towards the middle of the main body 2. The backfolding of the second anchoring member 8 of FIG. 17 is located away from the middle of the main body 2.

The material concentration and/or material thickness in the implantable device 1 can be in sections differently, for example the material quantity at the rim area of the implantable device 1 is adapted to the desired mechanical properties. Particularly at the rim area a material concentration 27 is located for a partial reinforcement.

The first end 3 and/or the second end 4 of the main body 2 of the implantable device 1 of FIG. 17 has one or multiple slings or loops 21 interlaced with each other and/or located adjacent to each other and/or intertwined with each other. The slings or loops 21 can form a regular rim 28 or an irregular rim 29. The irregular rim 29 is for example formed by slings or loops 21 of different sizes, e.g. by slings or loops 21 with two different sizes. Advantageously the arrangement of slings or loops 21 with different sizes is regular, for example one big sling or loop 21 after three small slings or loops 21.

The main body of the implantable device 1 is in the first operating state (primary form) stent-like. The cross-section of the implantable device 1 is in the first operating state (primary form) particularly round or oval. In the second operating state (secondary form) of the implantable device 1 the cross-section is in the areas where no anchoring members 7, 8 are located round or oval and particularly also in areas where the anchoring members 7, 8 are located.

For example the diameter of the implantable device 1 is in the second operating state (secondary form) in the area outside of the anchoring members 7, 8 about 35 mm and the length of the implantable device 1 is in the second operating state (secondary form) maximal 50 mm.

The main body of the implantable device 1 can have one or more layers.

Figure 18:
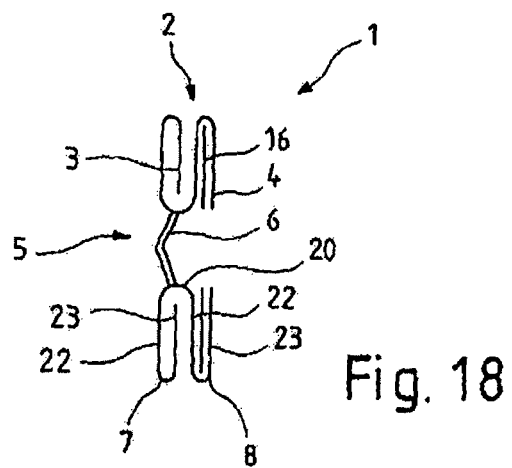

The $10^{th}$ embodiment of the inventive implantable device 1 shown in a sectional view in FIG. 18 differs from the $9^{th}$ embodiment of the inventive implantable device 1 of FIG. 17 in that the first membrane element 6 is located within the main body 2 between the first end 3 and the second end 4 of the main body. Particularly approximately in the middle in the longitudinal direction of the main body 2 between the first end 3 and the second end 4 of the main body 2. Furthermore in the $10^{th}$ embodiment according to FIG. 18 the second membrane element 16 is located at the second end 4 of the implantable device 1 between the first sub-portion 22 and the second sub-portion 23 of the second anchoring member 8.

Figure 19:
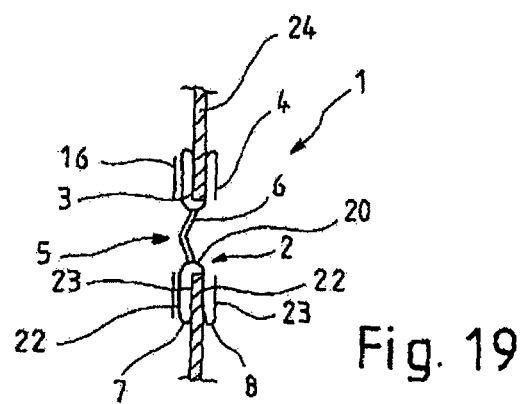

FIG. 19 shows a sectional view of an $11^{th}$ embodiment of an inventive implantable device 1 in an implanted state in a human or animal body 24. The $11^{th}$ embodiment according to FIG. 19 differs from the $10^{th}$ embodiment according to FIG. 18 in that the second membrane element 16 is located at the first end 3 of the implantable device 1. The second membrane element 16 and the first membrane element 6 are in the second operating state (secondary form) of the implantable device 1 adjacent to each other whereby particularly in the second flow direction a fluid tight connection is achieved.

Figure 20:
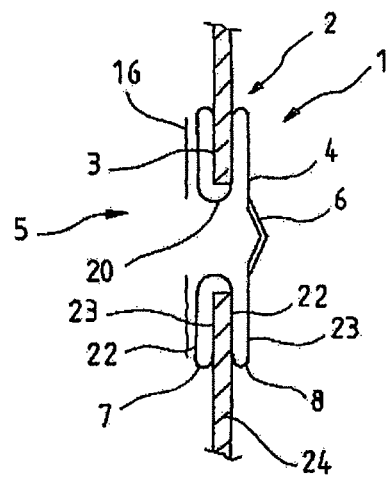

The $12^{th}$ embodiment of an inventive implantable device 1 in the implanted state is shown in FIG. 20. The $12^{th}$ embodiment of FIG. 20 differs from the $9^{th}$ embodiment of FIG. 17 in that the first membrane element is located in such a way that the first flow direction and the second flow direction of the $12^{th}$ embodiment are designed opposite to the $8^{th}$ embodiment of FIG. 17.

Figure 21:
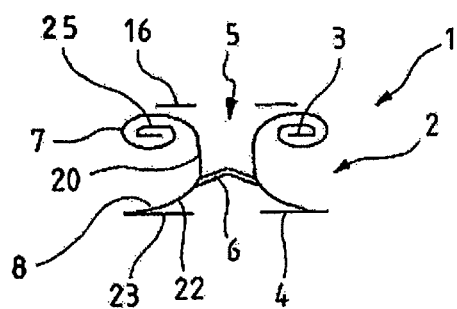

In FIG. 21 a $13^{th}$ embodiment of an inventive implantable device 1 for use in the human and/or animal body 24 to replace an organ valve is shown in a sectional view. The implantable device 1 comprises a main body 2 having a first end 3 and a second end 4, wherein the first end 3 and the second end 4 each have an opening 5 to provide a fluid connection through the main body 2 between the first end 3 and the second end 4 and a first membrane element 6 arranged inside of the main body 2, wherein the membrane element 6 is formed in such a manner that it allows the fluid connection through the main body 2 in a first flow direction and blocks the same in a second flow direction opposite the first flow direction. The main body 2 has in a first operating state (primary form) a large ratio of length to transverse expansion along the longitudinal axis of the main body 2 and in a second operating state (secondary form) a smaller ratio of length to transverse expansion along the longitudinal axis of the main body 2. The main body 2 is reversibly transferable from the secondary form to the primary form counter to elastic material forces by the application of a force. In FIG. 18 the implantable device 1 is shown in the second operating state (secondary form).

In the shown second operating state (secondary form) the main body 2 has at the first end 3 and the second end 4 each a radially outwardly of the main body 2 extending anchoring members 7, 8 for anchoring the device 1 in an organ and/or in a vessel.

The main body 2 of the implantable device 1 is formed from a single wire-like element 9 or from a plurality of wire-like elements 9 connected to each other by means of interlocking winding and/or twisting and/or weaving in the manner of a woven and/or layered fabric and/or net.

The radially outwardly of the main body extending anchoring members 7, 8 are circumferentially provided at the circumference of the main body 2 at the first end 3 and the second end 4.

According to the $5^{th}$ and $6^{th}$ embodiment from FIGS. 10 and 11 the $13^{th}$ embodiment according to FIG. 21 can also have areas of different rigidity 10, 11.

The main body 2 of the implantable device 1 of FIG. 21 can have at least one opening 12 in its circumferential wall, to provide a fluid connection between the inner of the main body 2 and a vessel of the human or animal body 24, particularly as disclosed with respect to the embodiments of FIGS. 12 and 13.

Advantageously the implantable device 1 of FIG. 21 consists completely or partially of a shape memory material, particularly of nitinol or a plastic with memory-shaped effect and comprises further at least one radio-opaque marker, particularly in the form of a marker tag, marking or marker wire. The implantable device 1 can also be completely or partially consist of an absorbable material.

The first membrane element 6 of the implantable device 1 of FIG. 21 consists of a synthetic or biological material and is particularly provided with a coating for establishing a biostability, particularly a titanium coating.

The main body 2 and the first membrane element 6 of the implantable device 1 are detachable or inseparable connected or connectable to each other, particularly by gluing, welding, sewing, fusing, dip-coating or another joining technology. The first membrane element 6 is in the second operating state (secondary form) located between the first end 3 and the second end 4 of the main body 2, particularly centrally in a longitudinal direction of the main body 2 between the first end 3 and the second end 4 of the main body 2.

The main body 2 of the implantable device 1 comprises in the second operating state (secondary form) at the first end 3 a second membrane element 16, to partially close the opening 5 at the first end 3 for fluids.

The implantable device 1 according to FIG. 1 is relocatable and explantable.

Furthermore the implantable device 1 of FIG. 21 is in the second operating state (secondary form) between the first end 3 and the second end 4 of the main body 2, thus particularly in the area of the intermediate member 20, at least partially, preferably completely deformable in a radial direction, such that the main body 2 can adapt to a vessel wall and/or circumference of an opening and/or edge of a defect opening.

The single wire-like element 9 of the implantable device 1 consists of a single wire 17, a wire strand 18 of at least two single wires or a multiple wire 19, as particularly disclosed with respect to the embodiments of FIGS. 14 to 16.

Both ends of the wire-like element 9 are located at the first end 3 or the second end 4 or in a side surface of the main body 2. Furthermore both ends of the wire-like element are connectable or connected to each other, particularly by using an additional element by twisting, gluing, welding, soldering or another joining technology.

The first anchoring member 7 of the implantable device 1 is in the second operating state (secondary form) located at the first end 3 of the main body 2 and the second anchoring member 8 is located at the second end 4 of the main body 2. The second anchoring member 8 is in the second operating state (secondary form) umbrella-shaped, as shown in FIG. 21. The second anchoring member 8 has in the second operating state (secondary form) of the main body a first sub-portion 22 and a second sub-portion 23, wherein the first sub-portion 22 extends in a radial direction of the main body 2 outwardly and the second sub-portion 23 is folded backwards in a radial direction of the main body 2 inwardly, particularly in such a way, that the first sub-portion 22 and the second sub-portion 23 are folded onto another to a double-layer.

As shown in FIG. 21 the first anchoring member 7 is in the second operating state (secondary form) of the main body 2 coiled, particularly helical. The coiling of the first anchoring member 7 is directed towards the middle of the main body 2.

As already disclosed with respect to the previous embodiments the material concentration 27 and/or the material thickness within the implantable device 1 can differ partially. Particularly the material quantity at the rim area of the implantable device 1 is adapted to the desired mechanical properties, particularly at the rim area of the implantable device 1 a material concentration 27 is located for a partial reinforcement.

The first end 3 or the second end 4 of the main body 2 of the implantable device 1 has advantageously one or multiple slings or loops 21 interlaced with each other and/or located adjacent to each other and/or intertwined with each other. The slings or loops 21 form a regular rim 28 or an irregular rim 29. An irregular rim 29 is formed by slings or loops 21 of different sizes, for example by slings or loops 21 with two different sizes. The arrangement of slings or loops 21 with different sizes can be regular, for example one big sling or loop 21 after three small slings or loops 21.

In the not shown first operating state (primary form) the main body 2 of the implantable device 1 of FIG. 21 is stent-like and has a round or oval cross-section.

In the second operating state (secondary form) the implantable device 1 of FIG. 21 has in areas, where no anchoring members are located a round or oval cross-sections. The shown implantable device 1 has in the second operating state (secondary form) in areas outside of the anchoring members 7, 8 a diameter of about 35 mm and a maximal length of 50 mm.

The main body 2 of the implantable device 1 of FIG. 21 can have one or multiple layers.

Figure 22:
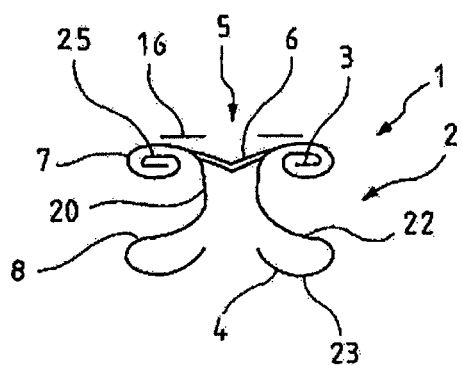

FIG. 22 shows a sectional view of a 14$^{th}$ embodiment of an inventive implantable device 1 for use in the human and/or animal body 24 to replace an organ valve. The 14$^{th}$ embodiment according to FIG. 22 differs from the 13$^{th}$ embodiment according to FIG. 21 on the one hand in that the first membrane element 6 is located at the first end 3 of the implantable device 1 in the second operating state (secondary form). On the other hand the implantable device 1 according to FIG. 22 comprises a second membrane element 16, which in the second operating state (secondary form) is located at the first end 3 of the implantable device 1. The first membrane element 6 and the second membrane element 16 are located adjacent to each other at the first end 3 of the main body 2 in the second operating state (secondary form). Thereby particularly the fluid tightness of the implantable device 1 at the first end is improved.

Furthermore the 14$^{th}$ embodiment according to FIG. 22 differs from the 13$^{th}$ embodiment from FIG. 21 in that the second anchoring member 8 is bulgy. Thereby it is achieved that the second anchoring member 8 is deformable and for example better conforms to a vessel wall or the inner wall of a heart ventricle.

Figure 23:
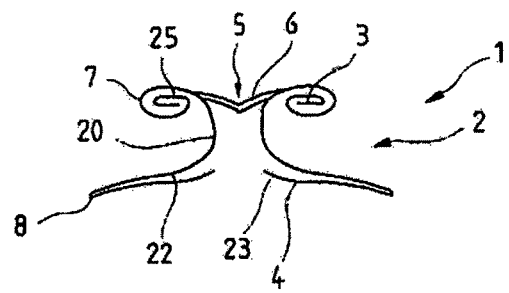

In FIG. 23 a sectional view of a 15$^{th}$ embodiment of an inventive implantable device 1 for use in the human or animal 24 to replace an organ valve is shown. The 15$^{th}$ embodiment according to FIG. 23 differs from the 14$^{th}$ embodiment according to FIG. 22 in that the second membrane element 16 is located at the first end 3 of the implantable device 1. Furthermore the second anchoring member 8 at the second end 4 of the main body 2 is curved in the second operating state (secondary form). A curvature of the second anchoring member 8 is located away from the middle of the main body 2 such that the apex of the curvature is directed towards the intermediate member 20 of the main body 2.

Furthermore the diameter of the second anchoring member 8 is larger than the diameter of the first anchoring member.

Figure 24:
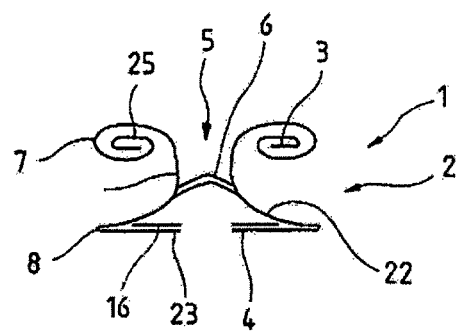

A 16$^{th}$ embodiment of an inventive implantable device 1 for use in the human or animal body 24 to replace an organ valve is shown in FIG. 24 in a sectional view. The 16$^{th}$ embodiment according to FIG. 24 differs from the 13$^{th}$ embodiment from FIG. 21 in that the second membrane element 16 is located within the backfolding of the second anchoring member 8. Because of the second membrane element 16 within the backfolding of the second anchoring member 8 the fluid tightness in the area of the second end 4 of the main body 2 is improved.

Figure 25:
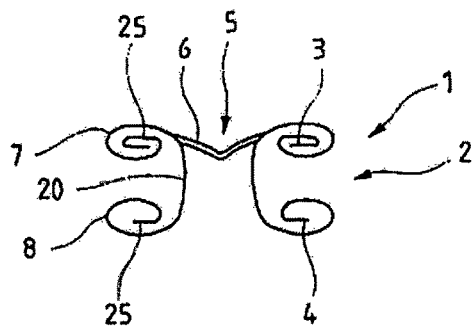

FIG. 25 shows a sectional view of a 17$^{th}$ embodiment of an inventive implantable device 1 for use in the human or animal body 24 to replace an organ valve. The 17$^{th}$ embodiment according to FIG. 25 differs from the 15$^{th}$ embodiment according to FIG. 23 in that the second anchoring member 8 also is built by a coiling 25 of the main body 2.

Figure 26:
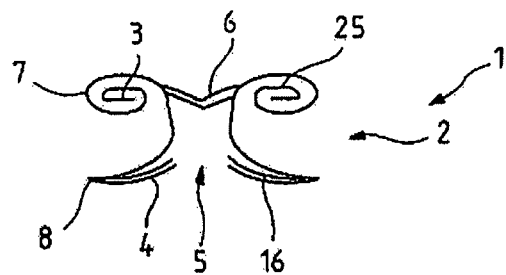

The sectional view of an 18$^{th}$ embodiment of an inventive implantable device 1 for use in the human or animal body 24 to replace an organ valve shown in FIG. 26 differs from the 15$^{th}$ embodiment of an inventive implantable device 1 from FIG. 23 by the curvature of the second anchoring member 8, the second membrane element 16 located within the backfolding of the second anchoring member 8 and the dimension of the second anchoring member 8. The curvature of the second anchoring member 8 of the implantable device 1 according to FIG. 26 is located towards the middle of the main body 2.

Figure 27:
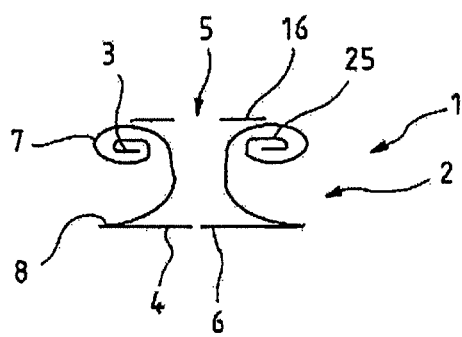

FIG. 27 shows a sectional view of a 19$^{th}$ embodiment of an inventive implantable device 1 for use in the human or animal body 24 to replace an organ valve. The 19$^{th}$ embodiment according to FIG. 27 differs from the 13$^{th}$ embodiment according to FIG. 21 in that the first membrane element 6 at the second end 4 of the main body 2 is integrally formed with the main body 2.

Figure 28:
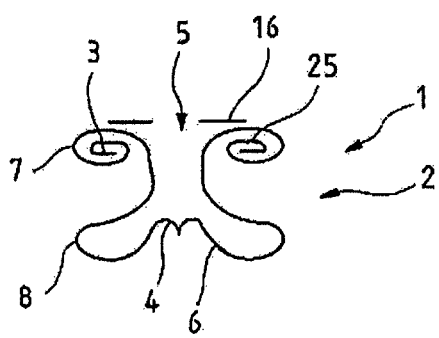

The sectional view of a 20$^{th}$ embodiment of an inventive implantable device 1 for use in the human or animal body 24 to replace an organ valve shown in FIG. 28 differs from the 19$^{th}$ embodiment of an inventive implantable device 1 according to FIG. 27 by the bulgy design of the second anchoring member 8.

The 21$^{st}$ embodiment of an inventive implantable device 1 for use in the human or animal body 24 to replace an organ valve, which is shown in FIG. 21 in a sectional view, differs from the 19$^{th}$ embodiment of an inventive implantable device 1 according to FIG. 27 by the curved design of the second anchoring member 8, wherein the curvature of the second anchoring member 8 is directed away from the middle of the main body 2. Furthermore the diameter of the second anchoring member 8 is larger than the diameter of the first anchoring member 7.

Figure 29:
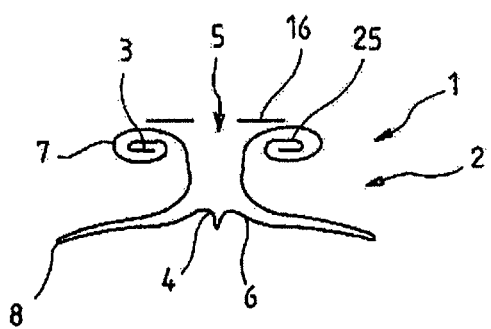
Figure 30:
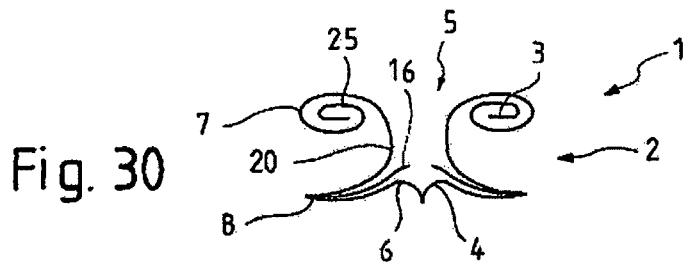

In FIG. 30 a sectional view of a 22$^{nd}$ embodiment of an inventive implantable device for use in the human or animal body 24 to replace an organ valve is shown in contrast to the 21$^{st}$ embodiment of the inventive implantable device 1 of FIG. 29 the curvature of the second anchoring member 8 is directed towards the middle of the main body 2. Furthermore within the double-layered anchoring member 8 a second membrane element 16 is located.

Figure 31:
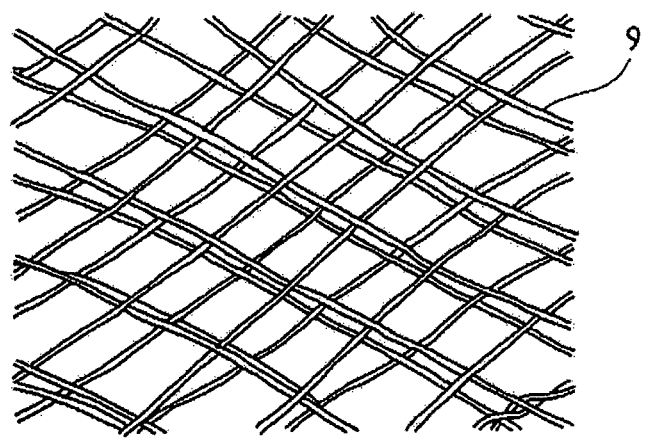
Figure 32:
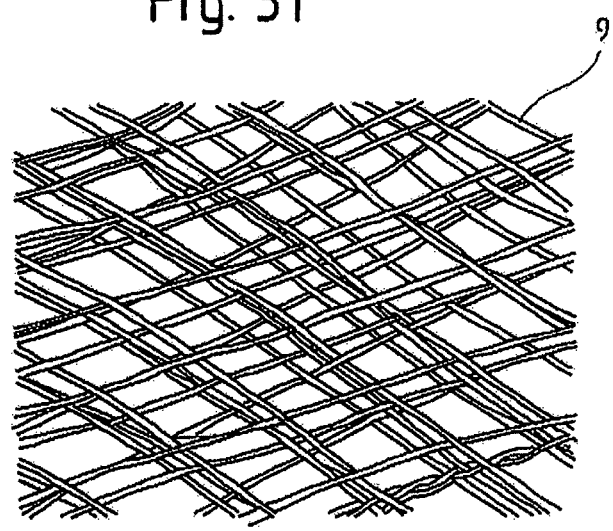

All of the previously described embodiments of the implantable device 1 for use in the human or animal body 24 to replace an organ valve can have one or multiple layers. In FIG. 31 a detailed view of a main body 2 of an inventive implantable device 1 with two layers is shown. FIG. 32 shows a detailed view of a main body 2 of an inventive implantable device 1 with three layers.

Figure 33:
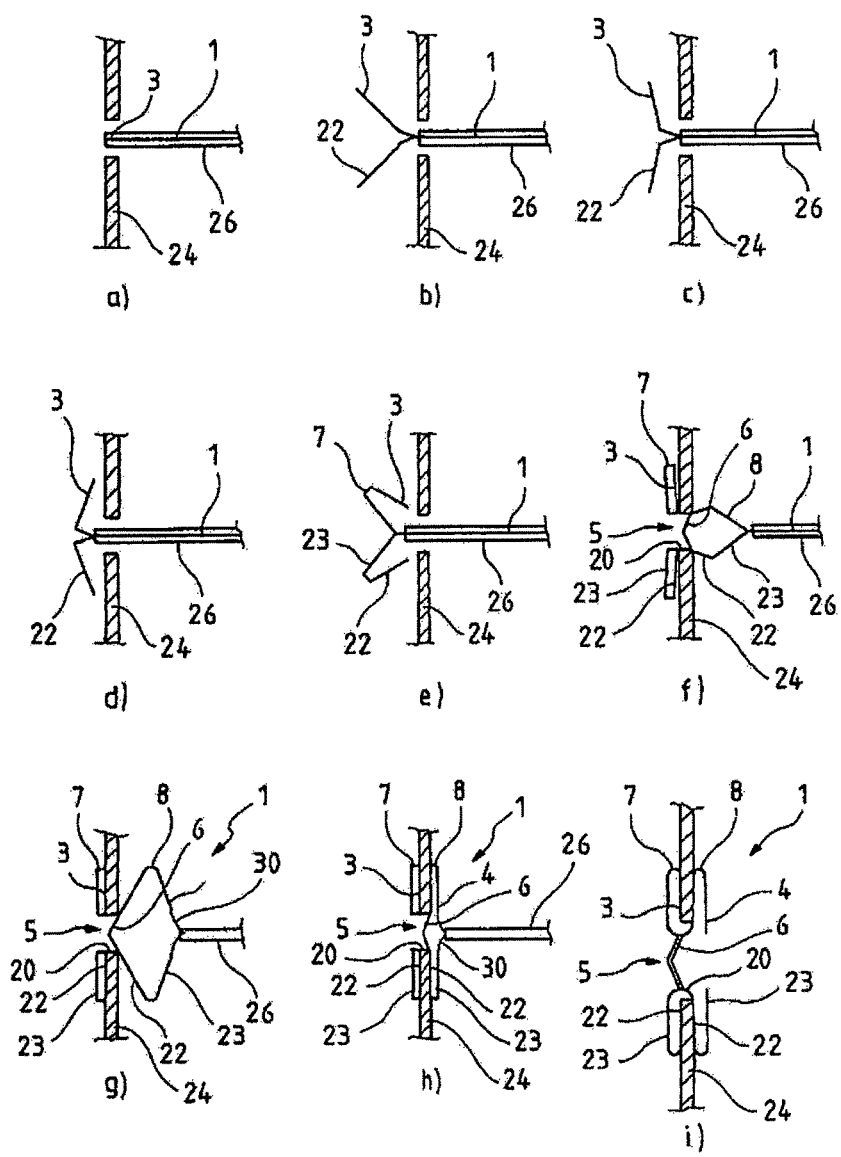

In FIG. 33 an exemplary implantation procedure of an inventive implantable device 1 for use in the human or animal body 24 to replace an organ valve is shown. The implantable device 1 is in a first operating state (primary form) stent-like and located within a catheter 26. The catheter 26 is for example directed via the venous system of the human or animal body 24 into the region of the implantation site. In FIG. 33a is shown how the end of catheter 26 is located within an opening in the human or animal body 24 into which the implantable device 1 should be implanted.

Afterwards the implantable device 1 is pushed out of catheter 26. Because the implantable device 1 consists of a memory shaped material and is reversibly transferred by a force against elastic material forces from the secondary form into the primary form, the implantable device 1 adapts after leaving catheter 26 the secondary form. In FIG. 33b is shown how the first end 3 of the implantable device 1 leaves catheter 26. The first end 3 of the implantable device 1, which first leaves the catheter 26, forms a first sub-portion 22 of the first anchoring member 7.

In FIG. 33c is shown how the first sub-portion 22 of the first anchoring member 7 has fully left the catheter and extends approximately rectangular to catheter 26 in a radial direction of the implantable device 1.

By further pushing out the implantable device 1 of the catheter 26 the backfolding of the first sub-portion 22 of the anchoring member 7 is formed and the second sub-portion 23 of the first anchoring member 7 exits catheter 26, as shown in FIGS. 33d and e.

As soon as the first anchoring member 7 is completely formed the catheter is retracted from the implantation site until the first anchoring member 7 rests against the surface of the human or animal body, particularly the first sub-portion 22 of the first anchoring member. The first sub-portion 22 and the second sub-portion 23 form the first anchoring member 7 with a backfolding such that the first anchoring member 7 is double-layered. Afterwards the inventive implantable device 1 is further pushed out of catheter 26, as shown in FIG. 33f. Furthermore, FIG. 33f shows that at the intermediate member 20 between the first anchoring member 7 and the second anchoring member 8 a first membrane element is located, wherein the membrane element 6 is formed in such a manner that it allows the fluid connections through the main body 2 in a first flow direction and block the same in a second flow direction opposite the first flow direction. The second anchoring member 8 of the implantable device 1 comprises also a first sub-portion 22 and a second sub-portion 23.

By further pushing out the implantable device 1 out of catheter 26 the second anchoring member 8 adopts the secondary form, wherein the first sub-portion 22 and the second sub-portion 23 of the second anchoring member 8 are also folded onto another to a double-layer. The backfolding of the first anchoring member 7 is in the direction of the opening in the human or animal body 24 and the backfolding of the second anchoring member 8 is located away from the opening in the human or animal body 24. FIG. 33g shows an implantable device 1 during the implantation with a completely formed first anchoring member 7 and a partially formed second anchoring member 8.

In FIG. 33h an implantable device 1 with completely formed first and second anchoring members 7, 8 is shown. The implantation of the implantable device 1 is carried out for example using guide wires 30 which are connected through the catheter 26 with the implantable device 1. In FIG. 33h is shown how the guide wires 30 are still connected to the second end 4 of the main body 2 of the implantable device 1. By retracting the guide wire 30 into catheter 26 the implantable device 1 can be retracted into catheter 26 and thereby be relocated or be explanted.

In case the implantable device 1 is placed within the opening of the human or animal body 24 as desired the guide wires are released from the implantable device 1 and the implantable device 1 remains within the human or animal body 24. The inventive implantable device 1 replaces for example a defect organ valve in the human or animal body 24.

Figure 34:
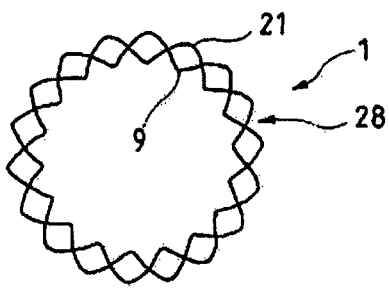

In FIG. 34 a detailed view of a first embodiment of a rim area of an implantable device 1 is shown. The rim area of the implantable device 1, thus the first end 3 or the second end 4 of the main body 2, is formed by multiple slings or loops 21 interlaced with each other and/or located adjacent to each other and/or intertwined with each other. In FIG. 34 the slings or loops 21 form a regular rim 28.

Figure 35:
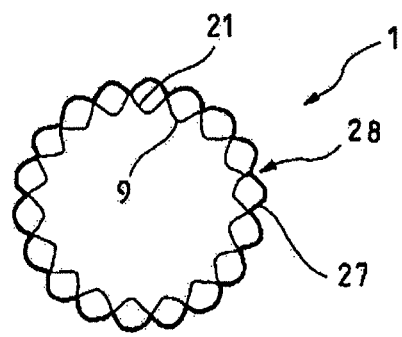

In FIG. 35 a detailed view of a second embodiment of a rim area of an inventive implantable device 1 is shown. The embodiment according to FIG. 35 differs from the embodiment according to FIG. 34 in that the implantable device 1 has sections with different material concentration and/or material thickness. According to FIG. 35 the rim area of the implantable device 1 has a material concentration 26 for a partial reinforcement.

Figure 36:
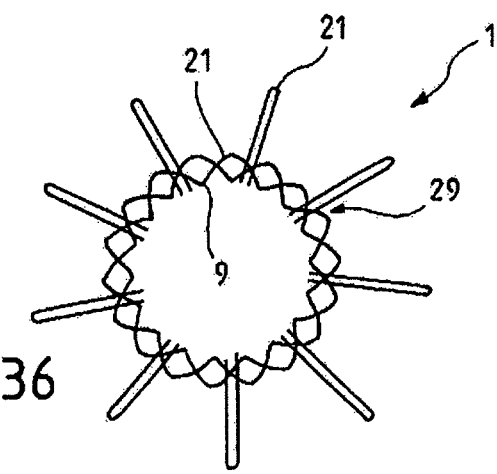

FIG. 36 shows a detailed view of the 3$^{rd}$ embodiment of a rim area of an inventive implantable device 1. The slings or loops 21 of the implantable device 1 according to FIG. 36 form an irregular rim 29. The irregular rim 29 is formed by slings or loops 21 with two different sizes. The arrangement of the different slings or loops 21 is regular in FIG. 36, namely one big loop or sling 21 after two small loops or slings 21. The embodiment according to FIG. 36 is particularly advantageous in case of a backfolding because the protruding big slings or loops 21 can engage for example into the capillary muscles of the heart during the backfolding of the rim area and thus anchor the implantable device 1 securely.

The previously enclosed embodiments of the inventive implantable device 1 are only illustrative for the invention and can be combined by the skilled person during his usual activity.

REFERENCE LIST 1 implantable device
2 main body
3 first end
4 second end
5 opening
6 first membrane element
7 first anchoring member
8 second anchoring member
9 wire-like element
10 area with lesser rigidity
11 area with higher rigidity
12 opening in circumferential wall
13 ring portion
14 valve portion
15 leaflet element
16 second membrane element
17 single wire
18 wire strand
19 multiple wire
20 intermediate member
21 slings/loops
22 first sub-portion
23 second sub-portion
24 human or animal body
25 coiling
26 catheter
27 material concentration
28 regular rim
29 irregular rim
30 guiding wire

What is claimed is:

1. An implantable device for use in the human and/or animal body to replace an organ valve, comprising:
   a main body having a first end and a second end, wherein the first end and the second end each have an opening to provide a fluid connection through the main body between the first end and the second end;
   a first membrane element arranged inside or at one end of the main body, wherein the membrane element is formed in such a manner that it allows the fluid connection through the main body in a first flow direction and blocks the same in a second flow direction opposite the first flow direction;
   wherein the main body has a large ratio of length to transverse expansion along the longitudinal axis of the main body in a first operating state (primary form) and a smaller ratio of length to transverse expansion along the longitudinal axis of the main body in a second operating state (secondary form);
   wherein the main body can be reversibly transferred from the secondary form to the primary form counter to elastic material forces by the application of a force;
   wherein the main body is formed from a single wire-like element or from a plurality of wire-like elements connected to each other by means of interlocking winding and/or twisting and/or weaving in the manner of a woven and/or layered fabric and/or net;
   wherein the main body in the second operating state (secondary form) has two anchoring members each extending in radial direction of the main body;
   wherein the first anchoring member is at the first end of the main body and the second anchoring member is at the second end of the main body;
   wherein the first end and/or the second end of the main body has one or multiple slings or loops interlaced with each other and/or located adjacent to each other and/or interwined with each other; and
   wherein the slings or loops form an irregular rim.

2. The implantable device according to claim 1, wherein the outwardly of the main body extending anchoring members are circumferentially provided at the circumference of the main body at the first end and second end.

3. The implantable device according to claim 1, wherein the implantable device has areas of different rigidity.

4. The implantable device according to claim 3, wherein the areas of different rigidity are formed by differently interlocking winding and/or twisting and/or weaving or by a wire-like element with different cross-sections, particularly round, oval and/or polygonal.

5. The implantable device according to claim 3, wherein, an area with lesser rigidity is located between areas with higher rigidity.

6. The implantable device according to claim 5, wherein the area with lesser rigidity is located at the main body outside of the at least on anchoring member.

7. The implantable device according to claim 1, wherein the implantable device comprises at least one radio-opaque marker, particularly in the form of a marker tag, marking or marker wire.

8. The implantable device according to claim 1, wherein the implantable device completely or partially consists of a shape memory material, particularly of Nitinol or a plastic with memory shape effect.

9. The implantable device according to claim 1, wherein the implantable device completely or partially consists of an absorbable material.

10. The implantable device according to claim 1, wherein the first membrane element consist of a synthetic or biological material, particularly of polyurethane.

11. The implantable device according to claim 1, wherein the first membrane element has a coating for establishing a biostability, particularly a titanium coating.

12. The implantable device according to claim 1, wherein the main body and the first membrane element are detachable or inseparable connected or connectable to each other, particularly by gluing, welding, sewing, fusing, dip-coating or another joining technology.

13. The implantable device according to claim 1, wherein the first membrane element has a ring portion and/or a valve portion connected to ring portion.

14. The implantable device according to claim 13, wherein the valve portion comprises three leaflet elements.

15. The implantable device according to claim 1, wherein the first membrane element is located in the second operating state (secondary form) at the first end of the main body, at the second end of the main body or between the first end and the second end of the main body, preferably centrally between the first end and the second end of the main body along the longitudinal axis of the main body.

16. The implantable device according to claim 1, wherein the main body has in the second operating state (secondary form) at the first end and/or at the second end at least a second membrane element, to partially close the opening at the first end and/or second end for fluids.

17. The implantable device according to claim 16, wherein the first membrane element and the second membrane element are located adjacent to each other at the first end of the main body or the second end of the main body.

18. The implantable device according to claim 1, wherein the implantable device is relocatable and/or explantable.

19. The implantable device according to claim 1, wherein the implantable device is in the second operating state (secondary form) between the first end and the second end of the main body at least partially, preferably completely, deformable in a radial direction, such that the main body can adapt to a vessel wall and/or circumference of an opening and/or edge of a defect organ valve.

20. The implantable device according to claim 1, wherein the multiple to each other connected wire-like elements consist of a single wire, a wire strand of at least two single wires and/or a multiple wire, particularly that the implantable device in areas with different rigidity consists of different wire-like elements, particularly of a single wire, a wire strand of at least two single wires and/or a multiple wire.

21. The implantable device according to claim 1, wherein the single wire-like element consists of a single wire, a wire strand of at least two single wires and/or a multiple wire.

22. The implantable device according to claim 1, wherein both ends of the wire-like element are located at the first end or the second end or in a side surface of the longitudinal main body.

23. The implantable device according to claim 1, wherein the at least one anchoring member is in the second operating state (Secondary form) disc-shaped or umbrella-shaped.

24. The implantable device according to claim 1, wherein the at least one or a further anchoring member is bulgy and/or curved.

25. The implantable device according to claim 1, wherein the main body has an intermediate member between the first anchoring member and the second anchoring member, which has a smaller diameter as the first anchoring member and the second anchoring member.

26. The implantable device according to claim 1, wherein the diameter of the two anchoring members is equal or different.

27. The implantable device according to claim 1, wherein the at least one anchoring member in the second operating state (secondary form) of the main body has a first sub-portion and a second sub-portion, wherein the first sub-portion extends in a radial direction of the main body outwardly and the second sub-portion is folded backwards in a radial direction of the main body inwardly or outwardly, particularly in such a way, that the first sub-portion and the second sub-portion are folded onto another to a double-layer.

28. The implantable device according to claim 27, wherein the backfolding or coiling of the at least one anchoring member is directed towards the middle of the main body or away from the middle of the main body.

29. The implantable device according to claim 1, wherein the at least one anchoring member is coiled in the second operating state (secondary form) of the main body, particularly helical.

30. The implantable device according to claim 1, wherein the material concentration and/or material thickness within the implantable device is in sections differently.

31. The implantable device according to claim 1, wherein the material quantity at the rim area of the implantable device is adapted to the desired mechanical properties, particularly at the rim area a material concentration is located for a partial reinforcement.

32. The implantable device according to claim 1, wherein the irregular rim is formed by slings or loops of different sizes.

33. The implantable device according to claim 32, wherein the irregular rim is formed by slings or loops of two different sizes.

34. The implantable device according to claim 33, wherein the arrangement of slings or loops with different sizes is regular, for example one big sling or loops after three small slings or loops.

35. The implantable device according to claim 1, wherein the main body in the first operating state (primary form) is stent like.

36. The implantable device according to claim 1, wherein both ends of the wire-like element are connectable or connected to each other, particularly by using an additional element, by twisting, gluing, welding, soldering, or another joining technology.

37. The implantable device according to claim 1, wherein the implantable device has a round or oval cross-section in the first operating state (primary form).

38. The implantable device according to claim 1, wherein the implantable device in the second operating state (secondary form) has a round or oval cross-sections in areas where no anchoring members are located.

39. The implantable device according to claim 1, wherein the diameter of the implantable device in the second operating state (secondary form) in areas outside of the anchoring members is about 35 mm.

40. The implantable device according to claim 1, wherein the length of the implantable device in the second operating state (secondary form) is max 50 mm.

41. The implantable device according to claim 1, wherein the main body has one or multiple layers.

42. The implantable device according to claim 1, wherein the main body and the first membrane element are built integrally.

* * * * *